United States Patent [19]

Prevatt et al.

[11] Patent Number: 5,330,901
[45] Date of Patent: Jul. 19, 1994

[54] **EXPRESSION OF HUMAN SERUM ALBUMIN IN *PICHIA PASTORIS***

[75] Inventors: William D. Prevatt; Kotikanyadan Sreekrishna, both of Bartlesville, Okla.

[73] Assignee: Research Corporation Technologies, Inc., Tucson, Ariz.

[21] Appl. No.: 691,079

[22] Filed: Apr. 25, 1991

[51] Int. Cl.⁵ .................. C12P 21/02; C12N 1/19
[52] U.S. Cl. .................. 435/69.6; 435/254.23; 935/37
[58] Field of Search ............ 435/69.1, 69.6, 71.1, 435/172.1, 183, 252.3, 320.1, 254.23; 935/22, 28, 33, 37, 66, 69

[56] References Cited

U.S. PATENT DOCUMENTS

| | | | |
|---|---|---|---|
| 4,414,329 | 11/1983 | Wegner | 435/71.1 |
| 4,775,622 | 10/1988 | Hitzeman | 435/69.4 |
| 4,808,537 | 2/1989 | Stroman et al. | 435/6 |
| 4,837,148 | 6/1989 | Cregg | 435/172.3 |
| 4,855,231 | 8/1989 | Stroman et al | 435/69.1 |
| 4,882,279 | 11/1989 | Cregg | 435/172.3 |
| 4,885,242 | 12/1989 | Cregg | 435/69.1 |
| 4,895,800 | 1/1990 | Tschopp et al. | 435/69.3 |

FOREIGN PATENT DOCUMENTS

| | | | |
|---|---|---|---|
| 73646 | 3/1983 | European Pat. Off. | C12N 15/00 |
| 206733 | 12/1986 | European Pat. Off. | C12N 15/00 |
| 248637 | 12/1987 | European Pat. Off. | C12N 15/00 |
| 251744 | 1/1988 | European Pat. Off. | C12N 15/00 |
| 256421 | 2/1988 | European Pat. Off. | C12N 15/00 |
| 344459 | 12/1989 | European Pat. Off. | C12N 15/00 |

OTHER PUBLICATIONS

*Chemical Abstracts, vol. 107, Jul. 6, 1987, p. 533, Abstract No. 5669.

Takahashi et al., PNAS, vol. 84, 1987, pp. 4413–4417.
Dugaiczyk et al., PNAS, vol. 79, 1982, pp. 71–75.
Latta et al., Bio/Technology, vol. 6, 1987, pp. 1309–1314.
Saunders et al., J. Bacteriol., vol. 169, 1987, pp. 2917–2925.
Lawn et al., Nuc. Acids Res., vol. 9, 1981, pp. 6103–6114.
Etcheverry et al., Bio/Technology, vol. 4, 1986, pp. 726–730.
Peters et al., in *Albumins: Structure, Biosynthesis, Function,* 1977, pp. 11–17.
Derwent Abstract of EP 123544, Oct. 1984.
Derwent Abstract of EP 91527, Oct. 1983.
Derwent Abstract of EP 201239, Nov. 1986.
Derwent Abstract of JP 60248181, Dec. 1985.
Sleep et al. "The secretion of human serum albumin from the yeast *S. cerevisiae* using five different leader sequences" Bio/Technology 8:42–46 (Jan. 1990).
Digan et al. "Secretion of heterologous proteins from the methylotrophic yeast, *Pichia pastoris*" Developments in Industrial Microbiology 29 (supp. 3):59–65 (1988).
ATCC catalogue of Fungi/Yeasts, 17th ed., 1987, ATCC, Rockville, Maryland, pp. 291, 413.
Difco Manual: Dehydrated Culture Media and Reagents, 1984, Difco, Detroit, Michigan, pp. 1131–1133.

*Primary Examiner*—Richard A. Schwartz
*Assistant Examiner*—J. Ketter
*Attorney, Agent, or Firm*—Scully, Scott, Murphy & Presser

[57] ABSTRACT

A process for the production of HSA in *Pichia pastoris* cells comprising cultivating *Pichia pastoris* cells capable of expressing HSA at a pH of about 5.7 to about 6.4 contemporaneously with the expression of HSA.

16 Claims, 6 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 940 bp
        ( B ) TYPE: nucleic acid
        ( C ) STRANDEDNESS: single
        ( D ) TOPOLOGY: linear ( i i ) MOLECULE TYPE: Genomic DNA ( i x ) SEQUENCE DESCRIPTION: SEQ ID NO:1:

```
AGATCTAACA  TCCAAAGACG  AAAGGTTGAA  TGAAACCTTT  TTGCCATCCG  ACATCCACAG      60
GTCCATTCTC  ACACATAAGT  GCCAAACGCA  ACAGGAGGGG  ATACACTAGC  AGCAGACCGT     120
TGCAAACGCA  GGACCTCCAC  TCCTCTTCTC  CTCAACACCC  ACTTTTGCCA  TCGAAAAACC     180
AGCCCAGTTA  TTGGGCTTGA  TTGGAGCTCG  CTCATTCCAA  TTCCTTCTAT  TAGGCTACTA     240
ACACCATGAC  TTTATTAGCC  TGTCTATCCT  GGCCCCCTG   GCGAGGTTCA  TGTTTGTTTA     300
TTTCCGAATG  CAACAAGCTC  CGCATTACAC  CCGAACATCA  CTCCAGATGA  GGGCTTTCTG     360
AGTGTGGGGT  CAAATAGTTT  CATGTTCCCC  AAATGGCCCA  AAACTGACAG  TTTAAACGCT     420
GTCTTGGAAC  CTAATATGAC  AAAAGCGTGA  TCTCATCCAA  GATGAACTAA  GTTTGGTTCG     480
TTGAAATGCT  AACGGCCAGT  TGGTCAAAAA  GAAACTTCCA  AAAGTCGGCA  TACCGTTTGT     540
CTTGTTTGGT  ATTGATTGAC  GAATGCTCAA  AAATAATCTC  ATTAATGCTT  AGCGCAGTCT     600
CTCTATCGCT  TCTGAACCCC  GGTGCACCTG  TGCCGAAACG  CAAATGGGGA  AACACCCGCT     660
TTTTGGATGA  TTATGCATTG  TCTCCACATT  GTATGCTTCC  AAGATTCTGG  TGGGAATACT     720
GCTGATAGCC  TAACGTTCAT  GATCAAAATT  TAACTGTTCT  AACCCCTACT  TGACAGCAAT     780
ATATAAACAG  AAGGAAGCTG  CCCTGTCTTA  AACCTTTTT   TTTATCATCA  TTATTAGCTT     840
ACTTTCATAA  TTGCGACTGG  TTCCAATTGA  CAAGCTTTTG  ATTTAACGA   CTTTTAACGA     900
CAACTTGAGA  AGATCAAAAA  ACAACTAATT  ATTCGAAACG                             940
```

( 2 ) INFORMATION FOR SEQ ID NO:2:

( i ) SEQUENCE CHARACTERISTICS:
        ( A ) LENGTH: 600 bp
        ( B ) TYPE: nucleic acid
        ( C ) STRANDEDNESS: single
        ( D ) TOPOLOGY: linear ( i i ) MOLECULE TYPE: Genomic DNA ( i x ) SEQUENCE DESCRIPTION: SEQ ID NO:2:

```
AAAGTAAACC  CCATTCAATG  TTCCGAGATT  TAGTATACTT  GCCCCTATAA  GAAACGAAGG      60
ATTTCAGCTT  CCTTACCCCA  TGAACAGAAA  TCTTCCATTT  ACCCCCCACT  GGAGAGATCC     120
GCCCAAACGA  ACAGATAATA  GAAAAAAGAA  ATTCGGACAA  ATAGAACACT  TTCTCAGCCA     180
ATTAAAGTCA  TTCCATGCAC  TCCCTTTAGC  TGCCGTTCCA  TCCCTTTGTT  GAGCAACACC     240
```

```
ATCGTTAGCC AGTACGAAAG AGGAAACTTA ACCGATACCT TGGAGAAATC TAAGGCGCGA    300

ATGAGTTTAG CCTAGATATC CTTAGTGAAG GGTGTTCCGA TACCTTCTCC ACATTCAGTC    360

ATAGATGGGC AGCTTTGTTA TCATGAAGAG ACGGAAACGG GCATTAAGGG TTAACCGCCA    420

AATTATATAA AAGACAACAT GTCCCCAGTT TAAAGTTTTT CTTTCCTATT CTTGTATCCT    480

GAGTGACCGT TGTGTTTAAT ATAACAAGTT CGTTTTAACT TAAGACCAAA ACCAGTTACA    540

ACAAATTATA ACCCCTCTAA ACACTAAAGT TCACTCTTAT CAAACTATCA AACATCAAAA    600
```

( 2 ) INFORMATION FOR SEQ ID NO:3:

( i ) SEQUENCE CHARACTERISTICS:
    ( A ) LENGTH: 1830 bp
    ( B ) TYPE: nucleic acid
    ( C ) STRANDEDNESS: single
    ( D ) TOPOLOGY: linear ( i i ) MOLECULE TYPE: Genomic DNA ( i x ) SEQUENCE DESCRIPTION: SEQ ID NO:3:

```
ATG  AAG  TGG  GTA  ACC  TTT  ATT  TCC  CTT  CTT  TTT  CTC  TTT  AGC  TCG
Met  Lys  Trp  Val  Thr  Phe  Ile  Ser  Leu  Leu  Phe  Leu  Phe  Ser  Ser
     -35            -30                      -25

GCT  TAT  TCC  AGG  GGT  GTG  TTT  CGT  CGA  GAT  GCA  CAC  AAG  AGT  GAG
Ala  Tyr  Ser  Arg  Gly  Val  Phe  Arg  Arg  Asp  Ala  His  Lys  Ser  Glu
     -20            -15                      -10

GTT  GCT  CAT  CGG  TTT  AAA  GAT  TTG  GGA  GAA  GAA  AAT  TTC  AAA  GCC
Val  Ala  His  Arg  Phe  Lys  Asp  Leu  Gly  Glu  Glu  Asn  Phe  Lys  Ala
     -5                  1                   5

TTG  GTG  TTG  ATT  GCC  TTT  GCT  CAG  TAT  CTT  CAG  CAG  TGT  CCA  TTT
Leu  Val  Leu  Ile  Ala  Phe  Ala  Gln  Tyr  Leu  Gln  Gln  Cys  Pro  Phe
10                  15                       20

GAA  GAT  CAT  GTA  AAA  TTA  GTG  AAT  GAA  GTA  ACT  GAA  TTT  GCA  AAA
Glu  Asp  His  Val  Lys  Leu  Val  Asn  Glu  Val  Thr  Glu  Phe  Ala  Lys
25                  30                       35

ACA  TGT  GTT  GCT  GAT  GAG  TCA  GCT  GAA  AAT  TGT  GAC  AAA  TCA  CTT
Thr  Cys  Val  Ala  Asp  Glu  Ser  Ala  Glu  Asn  Cys  Asp  Lys  Ser  Lue
40                  45                       50

CAT  ACC  CTT  TTT  GGA  GAC  AAA  TTA  TGC  ACA  GTT  GCA  ACT  CTT  CGT
His  Thr  Leu  Phe  Gly  Asp  Lys  Leu  Cys  Thr  Val  Ala  Thr  Leu  Arg
55                  60                       65

GAA  ACC  TAT  GGT  GAA  ATG  GCT  GAC  TGC  TGT  GCA  AAA  CAA  GAA  CCT
Glu  Thr  Tyr  Gly  Glu  Met  Ala  Asp  Cys  Cys  Ala  Lys  Gln  Glu  Pro
70                  75                       80

GAG  AGA  AAT  GAA  TGC  TTC  TTG  CAA  CAC  AAA  GAT  GAC  AAC  CCA  AAC
Glu  Arg  Asn  Glu  Cys  Phe  Leu  Gln  His  Lys  Asp  Asp  Asn  Pro  Asn
85                  90                       95

CTC  CCC  CGA  TTG  GTG  AGA  CCA  GAG  GTT  GAT  GTG  ATG  TGC  ACT  GCT
Leu  Pro  Arg  Leu  Val  Arg  Pro  Glu  Val  Asp  Val  Met  Cys  Thr  Ala
100                 105                      110

TTT  CAT  GAC  AAT  GAA  GAG  ACA  TTT  TTG  AAA  AAA  TAC  TTA  TAT  GAA
Phe  His  Asp  Asn  Glu  Glu  Thr  Phe  Leu  Lys  Lys  Tyr  Leu  Tyr  Glu
115                 120                      125

ATT  GCC  AGA  AGA  CAT  CCT  TAC  TTT  TAT  GCC  CCG  GAA  CTC  CTT  TTC
Ile  Ala  Arg  Arg  His  Pro  Tyr  Phe  Tyr  Ala  Pro  Glu  Leu  Leu  Phe
130                 135                      140

TTT  GCT  AAA  AGG  TAT  AAA  GCT  GCT  TTT  ACA  GAA  TGT  TGC  CAA  GCT
Phe  Ala  Lys  Arg  Tyr  Lys  Ala  Ala  Phe  Thr  Glu  Cys  Cys  Gln  Ala
145                 150                      155

GCT  GAT  AAA  GCT  GCC  TGC  CTG  TTG  CCA  AAG  CTC  GAT  GAA  CTT  CGG
Ala  Asp  Lys  Ala  Ala  Cys  Leu  Leu  Pro  Lys  Leu  Asp  Glu  Leu  Arg
160                 165                      170
```

-continued

| | | | | | | | | | | | | | |
|---|---|---|---|---|---|---|---|---|---|---|---|---|---|
| GAT | GAA | GGG | AAG | GTT | TCG | TCT | GCC | AAA | CAG | AGA | CTC | AAG | TGT | GCC |
| Asp 175 | Glu | Gly | Lys | Val | Ser 180 | Ser | Ala | Lys | Gln | Arg 185 | Leu | Lys | Cys | Ala |
| AGT | CTC | CAA | AAA | TTT | GGA | GAA | AGA | GCT | TTC | AAA | GCA | TGG | GCA | GTA |
| Ser 190 | Leu | Gln | Lys | Phe | Gly 195 | Glu | Arg | Ala | Phe | Lys 200 | Ala | Trp | Ala | Val |
| GCT | CGC | CTG | AGC | CAG | AGA | TTT | CCC | AAA | GCT | GAG | TTT | GCA | GAA | GTT |
| Ala 205 | Arg | Leu | Ser | Gln | Arg 210 | Phe | Pro | Lys | Ala | Glu 215 | Phe | Ala | Glu | Val |
| TCC | AAG | TTA | GTG | ACA | GAT | CTT | ACC | AAA | GTC | CAC | ACG | GAA | TGC | TGC |
| Ser 220 | Lys | Leu | Val | Thr | Asp 225 | Leu | Thr | Lys | Val | His 230 | Thr | Glu | Cys | Cys |
| CAT | GGA | GAT | CTG | CTT | GAA | TGT | GCT | GAT | GAC | AGG | GCG | GAC | CTT | GCC |
| His 235 | Gly | Asp | Leu | Leu | Glu 240 | Cys | Ala | Asp | Asp | Arg 245 | Ala | Asp | Leu | Ala |
| AAG | TAT | ATC | TGT | GAA | AAT | CAA | GAT | TCG | ATC | TCC | AGT | AAA | CTG | AAG |
| Lys 250 | Tyr | Ile | Cys | Glu | Asn 255 | Gln | Asp | Ser | Ile | Ser 260 | Ser | Lys | Leu | Lys |
| GAA | TGC | TGT | GAA | AAA | CCT | CTG | TTG | GAA | AAA | TCC | CAC | TGC | ATT | GCC |
| Glu 265 | Cys | Cys | Glu | Lys | Pro 270 | Leu | Leu | Glu | Lys | Ser 275 | His | Cys | Ile | Ala |
| GAA | GTG | GAA | AAT | GAT | GAG | ATG | CCT | GCT | GAC | TTG | CCT | TCA | TTA | GCT |
| Glu 280 | Val | Glu | Asn | Asp | Glu 285 | Met | Pro | Ala | Asp | Leu 290 | Pro | Ser | Leu | Ala |
| GCT | GAT | TTT | GTT | GAA | AGT | AAG | GAT | GTT | TGC | AAA | AAC | TAT | GCT | GAG |
| Ala 295 | Asp | Phe | Val | Glu | Ser 300 | Lys | Asp | Val | Cys | Lys 305 | Asn | Tyr | Ala | Glu |
| GCA | AAG | GAT | GTC | TTC | TTG | GGC | ATG | TTT | TTG | TAT | GAA | TAT | GCA | AGA |
| Ala 310 | Lys | Asp | Val | Phe | Leu 315 | Gly | Met | Phe | Leu | Tyr 320 | Glu | Tyr | Ala | Arg |
| AGG | CAT | CCT | GAT | TAC | TCT | GTC | GTG | CTG | CTG | CTG | AGA | CTT | GCC | AAG |
| Arg 325 | His | Pro | Asp | Tyr | Ser 330 | Val | Val | Leu | Leu | Leu 335 | Arg | Leu | Ala | Lys |
| ACA | TAT | GAA | ACC | ACT | CTA | GAG | AAG | TGC | TGT | GCC | GCT | GCA | GAT | CCT |
| Thr 340 | Tyr | Glu | Thr | Thr | Leu 345 | Glu | Lys | Cys | Cys | Ala 350 | Ala | Ala | Asp | Pro |
| CAT | GAA | TGC | TAT | GCC | AAA | GTG | TTC | GAT | GAA | TTT | AAA | CCT | CTT | GTG |
| His 355 | Glu | Cys | Tyr | Ala | Lys 360 | Val | Phe | Asp | Glu | Phe 365 | Lys | Pro | Leu | Val |
| GAA | GAG | CCT | CAG | AAT | TTA | ATC | AAA | CAA | AAT | TGT | GAG | CTT | TTT | GAG |
| Glu 370 | Glu | Pro | Gln | Asn | Leu 375 | Ile | Lys | Gln | Asn | Cys 380 | Glu | Leu | Phe | Glu |
| CAG | CTT | GGA | GAG | TAC | AAA | TTC | CAG | AAT | GCG | CTA | TTA | GTT | CGT | TAC |
| Gln 385 | Leu | Gly | Glu | Tyr | Lys 390 | Phe | Gln | Asn | Ala | Leu 395 | Leu | Val | Arg | Tyr |
| ACC | AAG | AAA | GTA | CCC | CAA | GTG | TCA | ACT | CCA | ACT | CTT | GTA | GAG | GTC |
| Thr 400 | Lys | Lys | Val | Pro | Gln 405 | Val | Ser | Thr | Pro | Thr 410 | Leu | Val | Glu | Val |
| TCA | AGA | AAC | CTA | GGA | AAA | GTG | GGC | AGC | AAA | TGT | TGT | AAA | CAT | CCT |
| Ser 415 | Arg | Asn | Leu | Gly | Lys 420 | Val | Gly | Ser | Lys | Cys 425 | Cys | Lys | His | Pro |
| GAA | GCA | AAA | AGA | ATG | CCC | TGT | GCA | GAA | GAC | TAT | CTA | TCC | GTG | GTC |
| Glu 430 | Ala | Lys | Arg | Met | Pro 435 | Cys | Ala | Glu | Asp | Tyr 440 | Leu | Ser | Val | Val |
| CTG | AAC | CAG | TTA | TGT | GTG | TTG | CAT | GAG | AAA | ACG | CCA | GTA | AGT | GAC |
| Leu 445 | Asn | Gln | Leu | Cys | Val 450 | Leu | His | Glu | Lys | Thr 455 | Pro | Val | Ser | Asp |
| AGA | GTC | ACC | AAA | TGC | TGC | ACA | GAA | TCC | TTG | GTG | AAC | AGG | CGA | CCA |
| Arg 460 | Val | Thr | Lys | Cys | Cys 465 | Thr | Glu | Ser | Leu | Val 470 | Asn | Arg | Arg | Pro |
| TGC | TTT | TCA | GCT | CTG | GAA | GTC | GAT | GAA | ACA | TAC | GTT | CCC | AAA | GAG |
| Cys | Phe | Ser | Ala | Leu | Glu | Val | Asp | Glu | Thr | Tyr | Val | Pro | Lys | Glu |

-continued

| 475 | | | | | 480 | | | | | 485 | | | |
|---|---|---|---|---|---|---|---|---|---|---|---|---|---|
| TTT | AAT | GCT | GAA | ACA | TTC | ACC | TTC | CAT | GCA | GAT | ATA | TGC | ACA | CTT |
| Phe | Asn | Ala | Glu | Thr | Phe | Thr | Phe | His | Ala | Asp | Ile | Cys | Thr | Leu |
| 490 | | | | | 495 | | | | | 500 | | | | |

| TCT | GAG | AAG | GAG | AGA | CAA | ATC | AAG | AAA | CAA | ACT | GCA | CTT | GTT | GAG |
| Ser | Glu | Lys | Glu | Arg | Gln | Ile | Lys | Lys | Gln | Thr | Ala | Leu | Val | Glu |
| 505 | | | | | 510 | | | | | 515 | | | | |

| CTT | GTG | AAA | CAC | AAG | CCC | AAG | GCA | ACA | AAA | GAG | CAA | CTG | AAA | GCT |
| Leu | Val | Lys | His | Lys | Pro | Lys | Ala | Thr | Lys | Glu | Gln | Leu | Lys | Ala |
| 520 | | | | | 525 | | | | | 530 | | | | |

| GTT | ATG | GAT | GAT | TTC | GCA | GCT | TTT | GTA | GAG | AAG | TGC | TGC | AAG | GCT |
| Val | Met | Asp | Asp | Phe | Ala | Ala | Phe | Val | Glu | Lys | Cys | Cys | Lys | Ala |
| 535 | | | | | 540 | | | | | 545 | | | | |

| GAC | GAT | AAG | GAG | ACC | TGC | TTT | GCC | GAG | GAG | GGT | AAA | AAA | CTT | GTT |
| Asp | Asp | Lys | Glu | Thr | Cys | Phe | Ala | Glu | Glu | Gly | Lys | Lys | Leu | Val |
| 550 | | | | | 555 | | | | | 560 | | | | |

| GCT | GCA | AGT | CAA | GCT | GCC | TTA | GGC | TTA | TAA | | | | | |
| Ala | Ala | Ser | Gln | Ala | Ala | Leu | Gly | Leu | - | | | | | |
| 565 | | | | | 570 | | | | | | | | | |

( 2 ) INFORMATION FOR SEQ ID NO:4:

( i ) SEQUENCE CHARACTERISTICS:
        ( A ) LENGTH: 16bp
        ( B ) TYPE: nucleic acid
        ( C ) STRANDEDNESS: single
        ( D ) TOPOLOGY: linear ( i i ) MOLECULE TYPE: Oligonucleotide ( i x ) SEQUENCE DESCRIPTION: SEQ ID NO:4:

CGAAACG ATG AAG TGG   16

Met Lys Trp ( 2 ) INFORMATION FOR SEQ ID NO:5:

( i ) SEQUENCE CHARACTERISTICS:
        ( A ) LENGTH: 19bp
        ( B ) TYPE: nucleic acid
        ( C ) STRANDEDNESS: single
        ( D ) TOPOLOGY: linear ( i i ) MOLECULE TYPE: Oligonucleotide ( i x ) SEQUENCE DESCRIPTION: SEQ ID NO:5:

GTTACCCACT TCATCGTTT   19

( 2 ) INFORMATION FOR SEQ ID NO:6:

( i ) SEQUENCE CHARACTERISTICS:
        ( A ) LENGTH: 13bp
        ( B ) TYPE: nucleic acid
        ( C ) STRANDEDNESS: single
        ( D ) TOPOLOGY: linear ( i i ) MOLECULE TYPE: Oligonucleotide ( i x ) SEQUENCE DESCRIPTION: SEQ ID NO:6:

TTAGGCTTAT AAG   13

( 2 ) INFORMATION FOR SEQ ID NO:7:

( i ) SEQUENCE CHARACTERISTICS:
        ( A ) LENGTH: 14bp
        ( B ) TYPE: nucleic acid
        ( C ) STRANDEDNESS: single
        ( D ) TOPOLOGY: linear (ii) MOLECULE TYPE: Oligonucleotide (ix) SEQUENCE DESCRIPTION: SEQ ID NO:7:

AATTCTTATA AGCC    14

(2) INFORMATION FOR SEQ ID NO:8:

(i) SEQUENCE CHARACTERISTICS:
 (A) LENGTH: 231bp
 (B) TYPE: nucleic acid
 (C) STRANDEDNESS: single
 (D) TOPOLOGY: linear (ii) MOLECULE TYPE: Linker Oligonucleotide (ix) SEQUENCE DESCRIPTION: SEQ ID NO:8:

CCTTAGGCTT ATAACATCTC TACATTTAAA AGCATCTCAG CCTACCATGA GAATAAGAGA    60

AAGAAAATGA AGATCAAAAG CTTATTCATC TGTGTTTTCT TTTTCGTTGG TGTAAAGCCA    120

ACACCCTGTC TAAAAAACAT AAATTTCTTT AATCATTTTG CCTCTTTTTC TCTGTGCTTC    180

AATTAATAAA AAATGGAAAG AATCTAAAAA AAAAAAAAAA AAAAGGAATT C             231

(2) INFORMATION FOR SEQ ID NO:9:

(i) SEQUENCE CHARACTERISTICS:
 (A) LENGTH: 20bp
 (B) TYPE: nucleic acid
 (C) STRANDEDNESS: single
 (D) TOPOLOGY: linear (ii) MOLECULE TYPE: Oligonucleotide (ix) SEQUENCE DESCRIPTION: SEQ ID NO:9:

CCTTAGGCTT ATAAGAATTC    20

EXPRESSION OF HUMAN SERUM ALBUMIN IN *PICHIA PASTORIS*

FIELD OF THE INVENTION

This invention relates to the field of recombinant DNA biotechnology. In one aspect, this invention relates to a process for the improved expression of secreted human serium albumin (HSA) in *Pichia pastoris*.

BACKGROUND

Human serum albumin is the most abundant plasma protein of adults. The concentration of albumin is 40 mg/ml, or 160 g of albumin circulating throughout the human body for a 70 Kg adult male. This protein maintains osmotic pressure and functions in the binding and transport of copper, nickel, calcium (weakly, at 2-3 binding sites), bilirubin and protoporphyrin, long-chain fatty acids, prostaglandins, steroid hormones (weak binding with these hormones promotes their transfer across the membranes), thyroxine, triiodothyronine, crystine, and glutathione. According to Peters, T. and Reed, R. G. in *Albumin: Structure, Biosynthesis and Function*, (Peter, T. and Sjoholm, J. eds.) 1977 p. 11-20, over 10,000 kilograms of purified albumin are administered annually in the United States alone to patients with circulatory failure or with albumin depletion.

Currently the only commercial source of HSA is from fractionated blood. Considering the possible dangers of blood borne contaminants and pathogens, it would be a considerable contribution to the commercial production of HSA to develop alternate methods of producing HSA. With the advent of recombinant DNA technology, it is now possible to produce HSA by alternate methods.

HSA has also been expressed in *Saccharomyces cerevisiae* as disclosed by Etcheverry et al. in *Bio/technology*, August 1986, p. 726 and Arjum Singh in EPA 123,544. Etcheverry disclosed HSA expression intracellularly in a concentration of approximately 6 mg/l and the secretion of HSA which remained cell associated. Arjum Singh also disclosed the expression of HSA in Saccharomyces cerevisiae in combination with the α-factor promoter and signal sequence. Singh appears to have been able to achieve an intracellular production level of approximately 25 mg/l and a secreted production level of 3 mg/l. *Pichia pastoris* has also been used to express HSA as is disclosed in EPA 344,459. The concentration of HSA produced in *Pichia pastoris* appears to be about 89 ng HSA/mg of protein. Although the process for producing HSA in recombinant expression system has been established by these experiments it would be desirable to optimize these processes to achieve the maximum possible HSA production.

Therefore, it would be a significant contribution to the art to provide a process for increasing the yeild of HSA from the recombinant expression of HSA in microorganism such as *Pichia pastoris*.

Therefore, it is an object of this invention to provide a process for increasing the yield of HSA produced in a recombinant expression systems.

SUMMARY OF THE INVENTION

In accordance, we have discovered a process for improving the secreted expression of HSA in *Pichia pastoris* cells comprising:

(a) cultivating in a fermentation broth transformed *Pichia pastoris* cells capable of expressing HSA under conditions suitable for the sustained viability of said *Pichia pastoris* cells under suitable conditions for the expression of HSA by said *Pichia pastoris* cells; and maintaining the pH of said fermentation broth from a pH of from about 5.7 to about 6.0 contemporaneously with the expression of HSA.

DETAILED DESCRIPTION OF THE FIGURES

Figure 1:
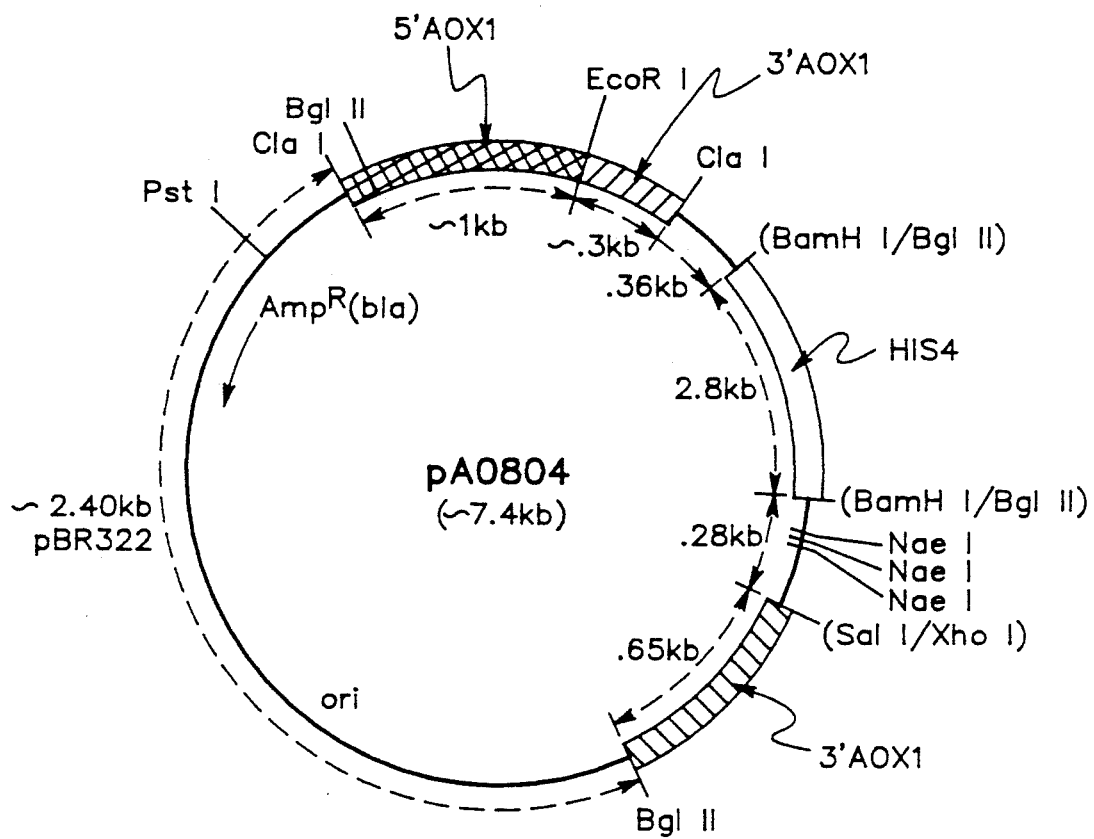

FIG. 1 provides a representation of plasmid pAO804 which contains a linear site-specific integrative vector in the fragment clockwise from BglII to BglII. The structural gene may be inserted in the unique EcoRI site of this plasmid. This plasmid may be recovered from the plasmid DNA of NRRL B-18114 by EcoRI digest and gel electrophoresis to recover a linear ~7.4 kb EcoRI fragment corresponding to FIG. 1.

Figure 2:
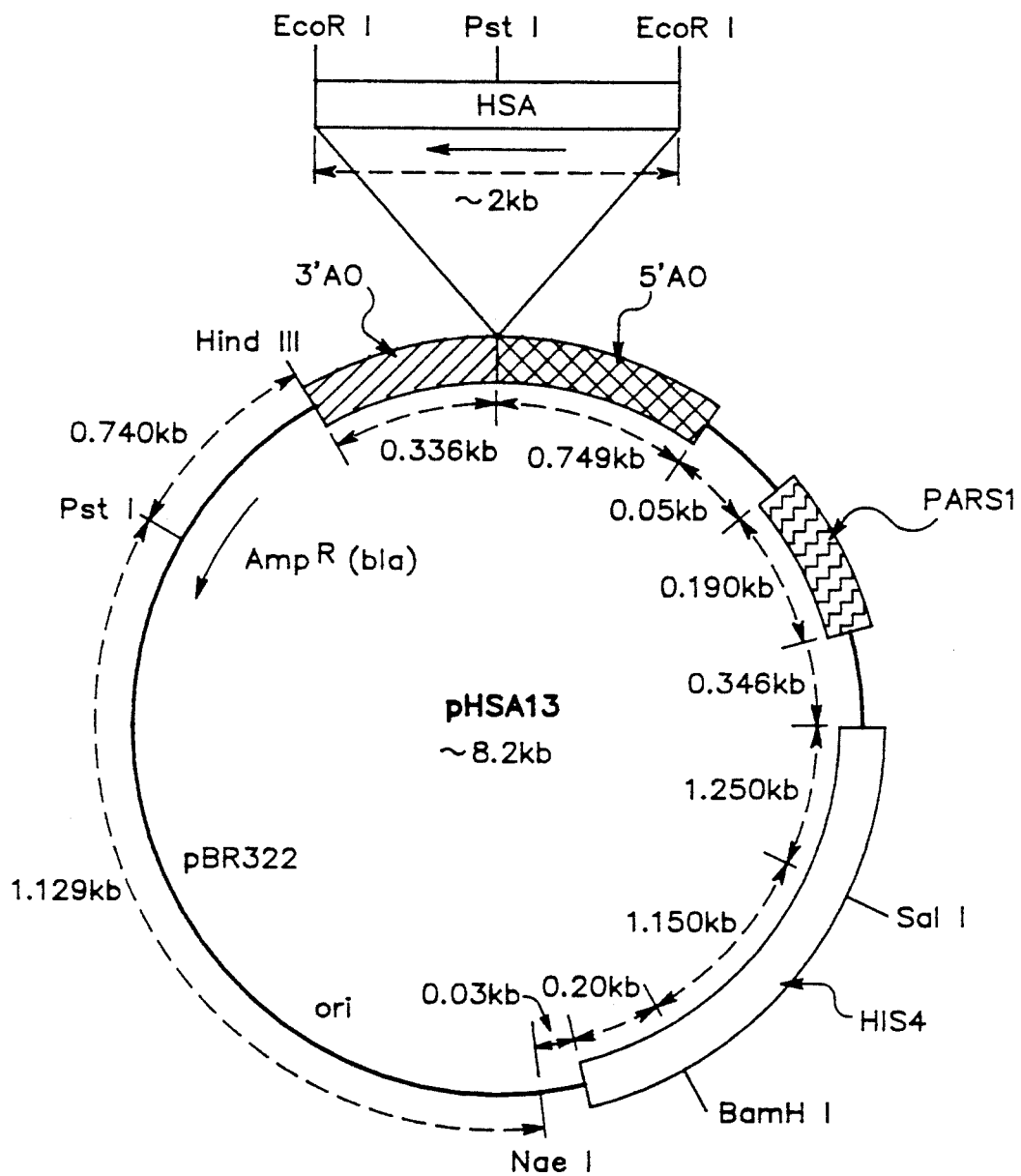

FIG. 2 provides a representation of pHSA13 in circular form.

Figure 3:
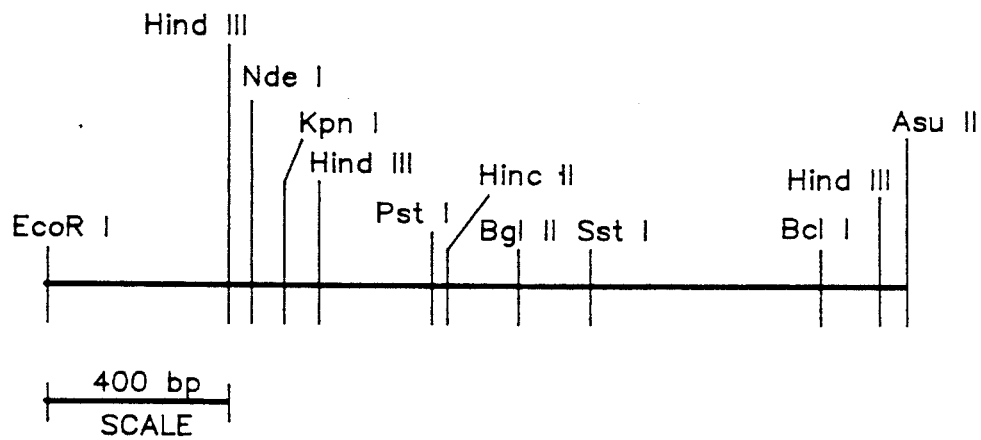

FIG. 3 provides a restriction map of the AOX1 5' regulatory region isolated from *Pichia pastoris*.

Figure 4:
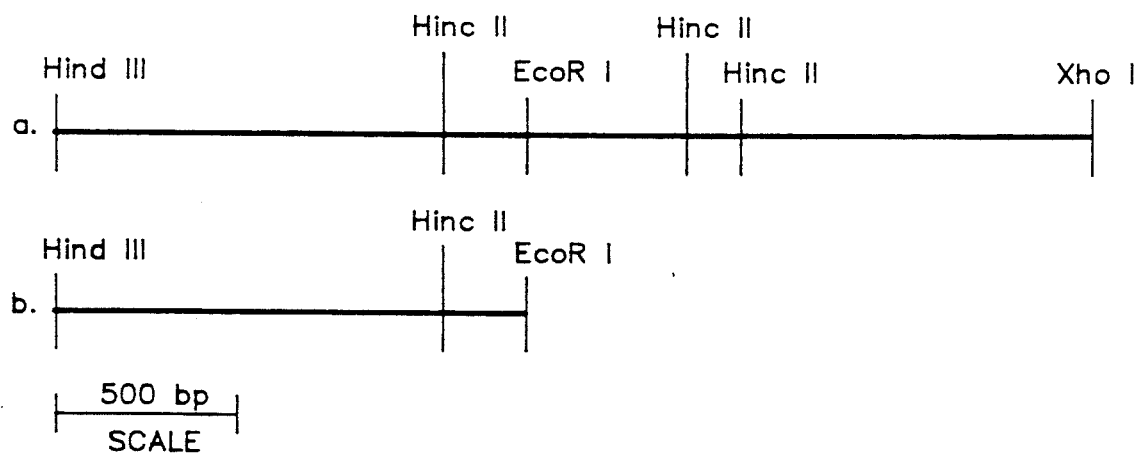

FIG. 4 provides a restriction map of the DAS1 5' regulatory region isolated from *Pichia pastoris*.

Figure 5:
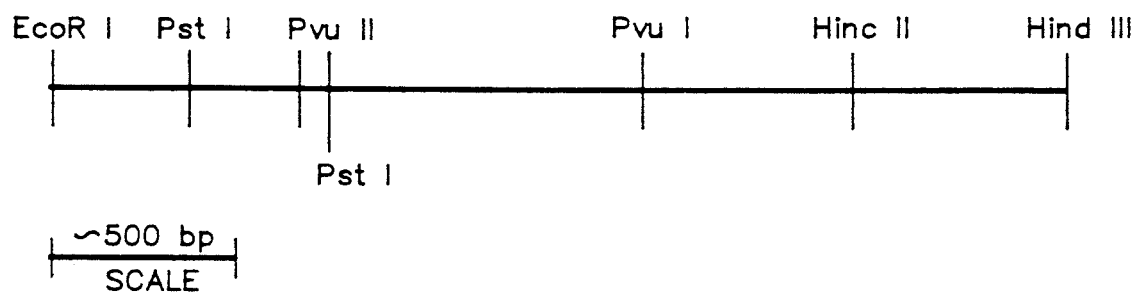

FIG. 5 provides a restriction map of the AOX1 3' termination sequence isolated from *Pichia pastoris*.

Figure 6:
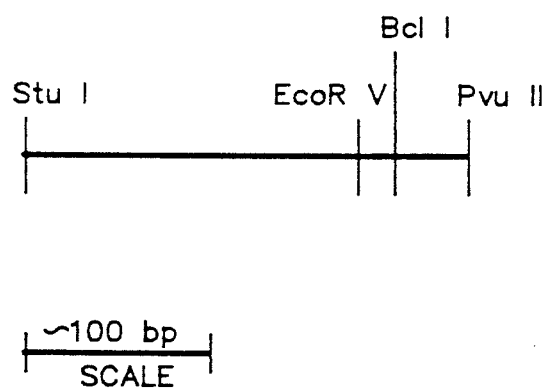

FIG. 6 provides a restriction map of the DAS1 3' termination sequence isolated from *Pichia pastoris*.

Figure 7:
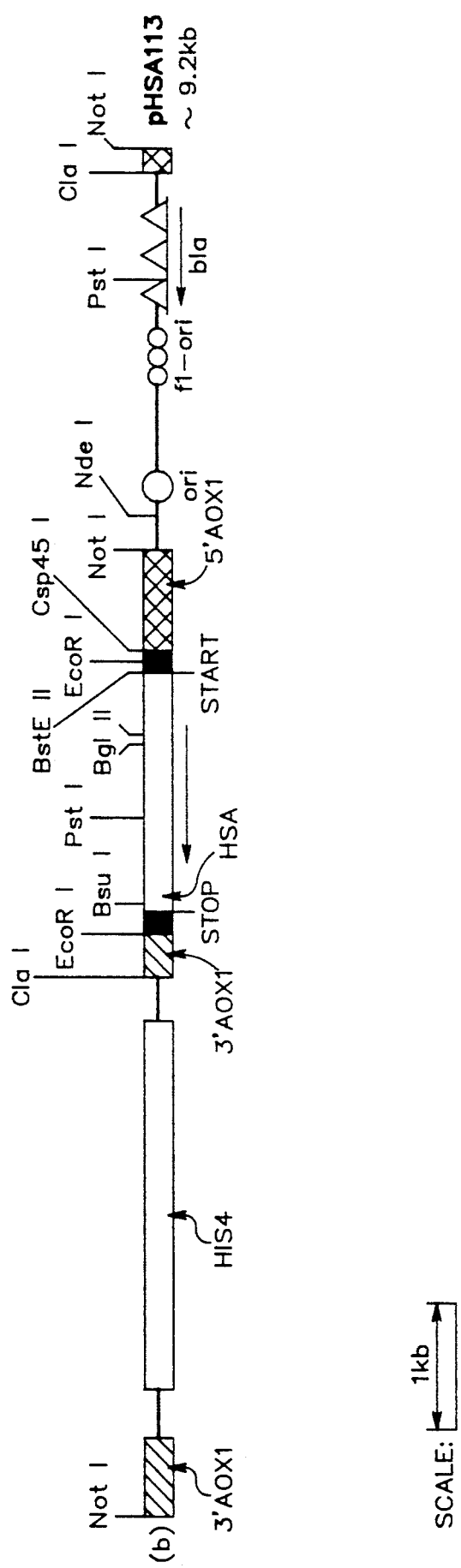

FIG. 7 provides a representation of pHSA113 in linear form.

Figure 8:
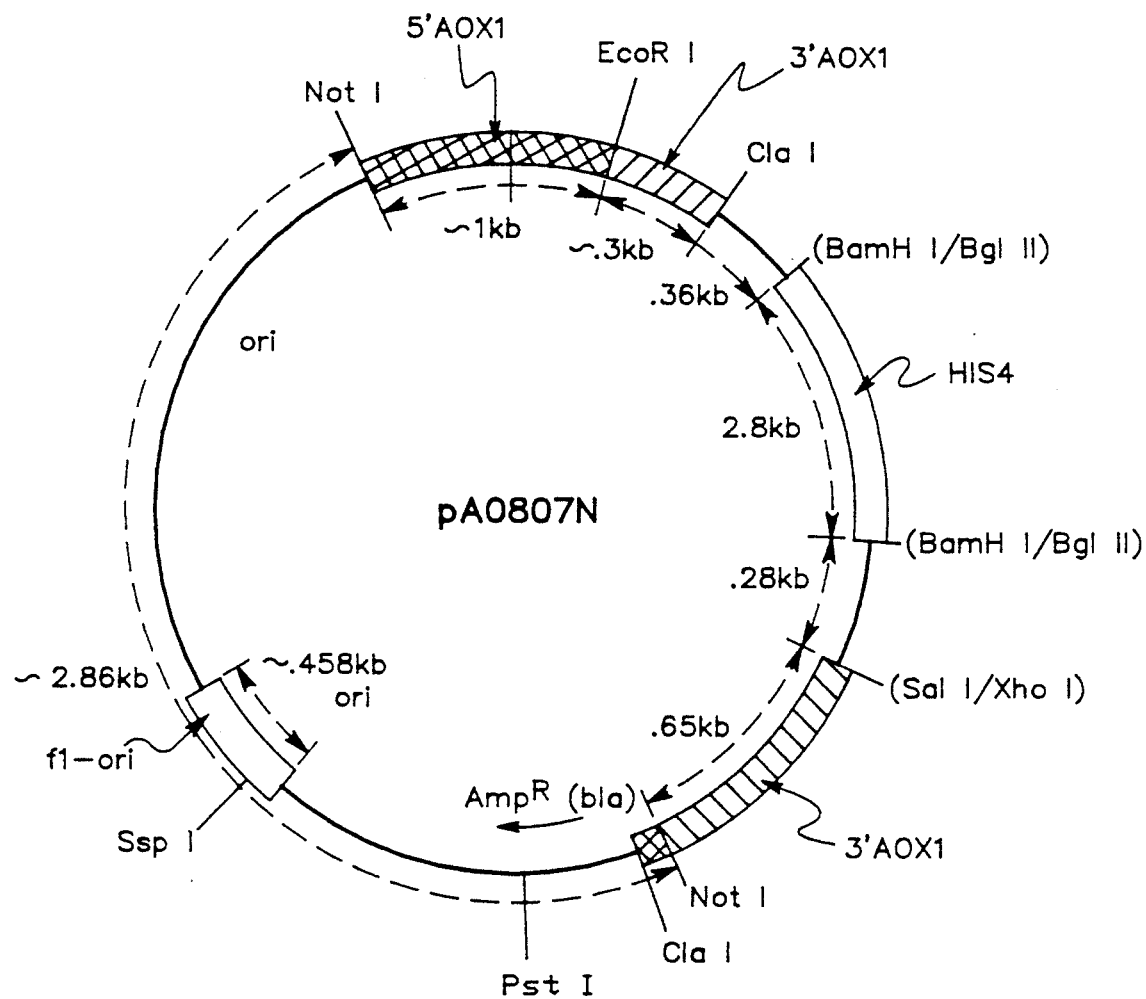

FIG. 8 provides a representation of plasmid pAO807N which contains a linear site-specific integrative vector in the fragment clockwise from NotI to NotI. The structural gene may be inserted in the unique EcoRI site of this plasmid.

DETAILED DESCRIPTION

Generally *Pichia pastoris* is optimally grown at from about pH 4.8 to about pH 5.2. Between this pH range *Pichia pastoris* provided with a suitable nutrient media exhibits robust growth. This pH range also appears to result in high levels of expression of several foreign proteins such as hepatitis B surface antigen. This pH range also appeared to provide high levels of expression with human serum albumin (HSA). For example growing *Pichia pastoris* cells which had been transformed with a vector containing a HSA structural gene operably linked to a 5' regulatory region (i.e. a promoter) and a 3' termination sequence, the expression levels of HSA which had been obtained were approximately 0.71 to 0.81 grams/liters of HSA in the fermentation broth. However, we have been able to further increase this yield by at least 50% by taking the unprecedented step of shifting the pH of the fermentation broth from about 5.2 to in the range of from about pH 5.7 to about pH 6.4, with a preferred pH range of from about pH 5.7 to about pH 6.0 and most preferably a pH in the range of from pH 5.75 to pH 5.85. The increased secretion levels obtained in the upper limits of the pH range (i.e. from in the range of pH 6.0 to pH 6.4) have been confirmed in shake tube optimization studies which indicate that the presence of yeast extract and peptone together with aeration will provide optimal HSA secretion in shake tubes. However, the use of yeast extract, peptone and excess aeration is not believed necessary in large scale fermentation where the pH can be continuously monitored. We believe that this higher pH level will increase the yield of any *Pichia pastoris* strain transformed with an expression cassette containing a promoter and a structural gene encoding a signal sequence and the mature HSA protein. Further it would appear that this result will be applicable to a variety of heterologous structural genes which encode a signal sequence and a mature heterologous protein. Suitable heterologous proteins which may be expressed at higher levels utilizing this method include but are not limited to heterologous proteins selected from the group consisting of tissue plasminogen activator, albumins (such as human serum albumin), lysozymes (such as bovine lysozyme), interferons (such as gamma-interferon and beta-interferon) and invertase. Each of the heterologous structural genes utilized in the present invention must have a signal sequence operably linked to the 5' end of sequence coding for the mature heterologous protein to effect the secretion of the mature protein. For example the tissue plasmigen activator, human serum albumins, bovine lysozyme, beta-interferon, gamma-interferon and invertase proteins may all be secreted utilizing the native signal sequence. Furthermore these proteins may also be secreted utilizing secretion signal sequences from *Pichia pastoris* such as the acid phosphatase signal sequence disclosed in U.S. patent application Ser. No. 07/627,539 filed Dec. 14, 1990 by Richard Buckholz assigned to Phillips Petroleum Company (incorporated herein by reference) or the alpha-mating factor signal sequence from *Saccharomyces cerevisiae*.

Utilizing the present invention, HSA secretion levels of approximately 1-3 grams of authentic HSA per liter of fermentation broth have been obtained. This invention thus provides a means for the high level secretion of HSA. Achieving these levels of HSA production is a significant advancement over the prior production levels, since at the level of 1-3 grams per liter the recovery of HSA in high yields with high purities is possible.

To express the HSA structural gene, the gene must be operably linked to a 5' regulatory region and a 3' termination sequence, which forms an expression cassette which will be inserted into a host (usually a microorganism) via a vector (such as a plasmid or linear site-specific integrative vector). Operably linked as used in this context refers to a juxtaposition wherein the 5' regulatory region, structural gene, and 3' termination sequence are linked and configured so as to perform their normal function. 5' regulatory region or promoter as used herein means DNA sequences which respond to various stimuli and provide enhanced rates of mRNA transcription. 3' termination sequence are sequences 3' to the stop codon of a structural gene which function to stabilize the mRNA transcription product of the gene to which the sequence is operably linked (such as sequences which elicit polyadenylation). For the practice of this invention, it is preferred that the ATG of the structural gene be linked with as few intervening deoxyribonucleotides as possible to the 3' end of the 5' regulatory region, preferrably about 11 or less deoxyribonucleotides and most preferably 8 or less deoxyribonucleotides. It is also preferred that the adenine and thymine content of the intervening deoxyribonucleotides be in the range of from about 55 percent to about 64 percent. Further, it appears that there are nucleotide preferences for certain specific locations. Counting left from the ATG condon of the structural gene with the first position left being the −1 position, it appears that adenine or cytosine is the most preferred deoxyribonucleotide, in the −2 position the most preferred deoxyribonucleotide is either adenine or thymine, in the −3 position the most preferred deoxyribonucleotide is adenine or thymine and the most preferred nucleotide at the −4 position is adenine, thymine or cytosine. Currently, it is preferred that the AOX1 or DAS1 5' regulatory region having the restriction maps of FIGS. 3 and 4 or, the sequences provided as SEQ ID No: 1 and SEQ ID No: 2, respectively, be linked at their 3' end of the sequence to the ATG start codon of the HSA structural gene. One example of an appropriate linkages for the AOX1 5' regulatory region is illustrated below:

TABLE I

| Construct Designation | End of the 5' Regulatory Region for AOX 1 | Deoxyribonucleotide intervening before ATG start condon |
|---|---|---|
| pHSA413 | 5' - TTCGAAACG | 5' - NONE |

Several 5' regulatory regions have been characterized and can be employed in conjunction with the expression of HSA in *Pichia pastoris*. Exemplary 5' regulatory regions are the primary alcohol oxidase (AOX1), dihydroxyacetone synthase (DAS1), glyceraldehyde-3-phosphate dehydrogenase gene (GAP), acid phosphatase gene (PHO1) and the p40 regulatory regions, derived from *Pichia pastoris* and the like. The AOX1 5' regulatory region, DAS1 5' regulatory region and p40 5' regulatory region are described in U.S. Pat. No. 4,855,231, incorporated herein by reference. The GAP 5' regulatory region is disclosed in EPA 374,913 published Jun. 27, 1990, incorporated herein by reference. The PHO1 5' regulatory region is disclosed in U.S. patent application 07/672,539 filed Dec. 14, 1990, assigned to Phillips Petroleum Company. The presently preferred 5' regulatory regions employed in the practice of this invention are those characterized by their ability to respond to methanol-containing media, such regulatory regions selected from the group consisting of AOX1, and DAS1. The most preferred 5' regulatory region for the practice of this invention is the AOX1 5' regulatory region.

3' termination sequences should be utilized in the expression cassette as discussed above. 3' termination sequences may function to terminate, polyadenylate and/or stabilize the messenger RNA coded for by the structural gene when operably linked to a gene, but the particular 3' termination sequence is not believed to be critical to the practice of the present invention. A few examples of illustrative sources for 3' termination sequences for the practice of this invention include but are not limited to the *Hansenula polymorpha* and *Pichia pastoris* 3' termination sequences. Preferred are those derived from *Pichia pastoris* such as those selected from the group consisting of the 3' termination sequences of AOX1 gene, DAS1 gene, p40 gene GAP gene, PHO1 gene and HIS4 gene. Particularly preferred is the 3' termination sequence of the AOX1 gene.

*Pichia pastoris* may be transformed with a variety of HSA structural genes (in the inventive transformants discussed herein the HSA structural gene encodes both a signal sequence and a mature HSA protein). HSA structural genes have been sequenced by Lawn et al. *Nuc. Acids Res.* 9:6105 (1981), and Dugaiczyk et al., *Proc. Natl. Acad. Sci.* USA 79:71 (1982). These genes may also be obtained by reisolation of the genes by the technique of Lawn et al., Dugaiczyk et al. or synthesized in vitro by a custom gene manufacturer such as British Biotechnology, Ltd. One possible method of obtaining a HSA gene would be to screen a human liver cDNA library with oligonucleotide probes or screen a human liver cDNA expression library with anti-HSA antisera to identify HSA expressing cDNAs. One suitable HSA structural gene is provided in SEQ ID NO: 3. Once a structural gene for HSA is recovered, it may be necessary to further tailor the gene. Following the isolation of an HSA structural gene, the gene is inserted into a suitable *Pichia pastoris* vector such as a plasmid or linear site-specific integrative vector.

Plasmid-type vectors have long been one of the basic elements employed in recombinant DNA technology. Plasmids are circular extra-chromosomal double-stranded DNA found in microorganisms. Plasmids have been found to occur in single or multiple copies per cell. Included in plasmid DNA is the information required for plasmid reproduction, e.g. an autonomous replication sequence such as those disclosed by James M. Cregg in U.S. Pat. No. 4,837,148, issued Jun. 6, 1989, incorporated herein by reference. Additionally one or more means of phenotypically selecting the plasmid in transformed cells may also be included in the information encoded in the plasmid.

Suitable integrative vectors for the practice of the present invention are the linear site-specific integrative vectors described by James M. Cregg, in U.S. Pat. NO. 4,882,279, issued Nov. 21, 1989, which is incorporated herein by reference. These vectors comprise a serially arranged sequence of at least 1) a first insertable DNA fragment; 2) a selectable marker gene; and 3) a second insertable DNA fragment. An expression cassette containing a heterologous structural gene is inserted in this vector between the first and second insertable DNA fragments either before or after the marker gene. Alternatively, an expression cassette can be formed in situ if a regulatory region or promoter is contained within one of the insertable fragments to which the structural gene may be operably linked.

The first and second insertable DNA fragments are each at least about 200 nucleotides in length and have nucleotide sequences which are homologous to portions of the genomic DNA of the species to be transformed. The various components of the integrative vector are serially arranged forming a linear fragment of DNA such that the expression cassette and the selectable marker gene are positioned between the 3' end of the first insertable DNA fragment and the 5' end of the second insertable DNA fragment. The first and second insertable DNA fragments are oriented with respect to one another in the serially arranged linear fragment as they are oriented in the parent genome.

Nucleotide sequences useful as the first and second insertable DNA fragments are nucleotide sequences which are homologous with separate portions of the native genomic site at which genomic modification is to occur. For example, if genomic modification is to occur at the locus of the alcohol oxidase gene, the first and second insertable DNA fragments employed would be homologous to separate portions of the alcohol oxidase gene locus. Examples of nucleotide sequences which could be used as first and second insertable DNA fragments are deoxyribonucleotide sequences selected from the group consisting of the *Pichia pastoris* alcohol oxidase (AOX1) gene, dihydroxyacetone synthase (DAS1) gene, p40 gene, glyceraldehyde-3-phosphate dehydrogenase (GAP) gene, acid phosphatase (PHO1) gene and HIS4 gene. The AOX1 gene, DAS1 gene, p40 gene and HIS4 genes are disclosed in U.S. Pat. Nos. 4,855,231 and 4,885,242 both incorporated herein by reference. The designation DAS1 is equivalent to the DAS designation originally used in U.S. Pat. Nos. 4,855,231 and 4,885,242. The GAP gene is disclosed in EPA 374,913 published Jun. 27, 1990 incorporated herein by reference. The PHO1 gene is disclosed in U.S. patent application Ser. No. 07/627,539 filed Dec. 14, 1990, now U.S. Pat. No. 5,268,273, assigned to Phillips Petroleum Company, incorporated herein by reference.

The first insertable DNA fragment may contain an operable regulatory region which may comprise the regulatory region utilized in the expression cassette. The use of the first insertable DNA fragment as the regulatory region for an expression cassette is a preferred embodiment of this invention. FIG. 1 provides a diagram of a vector utilizing the first insertable DNA fragment as a regulatory region for a cassette. Optionally, as shown in FIG. 1, an insertion site or sites and a 3' termination sequence may be placed immediately 3' to the first insertable DNA fragment. This conformation of the linear site-specific integrative vector has the additional advantage of providing a ready site for insertion of a structural gene without necessitating the separate addition of a compatible 3' termination sequence.

If the first insertable DNA fragment does not contain a regulatory region, a suitable regulatory region will need to be inserted linked to the structural gene, in order to provide an operable expression cassette. Similarly, if no 3' termination sequence is provided at the insertion site to complete the expression cassette, a 3' termination sequence can be operably linked to the 3' end of the structural gene.

It is also highly desirable to include at least one selectable marker gene in the DNA used to transform the host strain. This facilitates selection and isolation of those organisms which have incorporated the transforming DNA. The marker gene confers a phenotypic trait to the transformed organism which the host did not have, e.g. restoration of the ability to produce a specific amino acid where the untransformed host strain has a defect in the specific amino acid biosynthetic pathway, or provides resistance to antibiotics and the like. Exemplary selectable marker genes may be selected from the group consisting of the HIS4 gene (disclosed in U.S. Pat. No. 4,885,242) and the ARG4 gene (disclosed in U.S. Pat. No. 4,818,700 incorporated herein by reference) from *Pichia pastoris* and *Saccharomyces cerevisiae*, the invertase gene (SUC2) (disclosed in U.S. Pat. No. 4,857,467 incorporated herein by reference) from *Saccharomyces cerevisiae*, or the $G418^R$/kanamycin resistance gene from the *E. coli* transposable elements Tn601 or Tn903.

Those skilled in the art recognize that additional DNA sequences can also be incorporated into the vectors employed in the practice of the present invention, such as, for example, bacterial plasmid DNA, bacteriophage DNA, and the like. Such sequences enable the amplification and maintenance of these vectors in bacterial hosts.

The insertion of the HSA structural gene into suitable vectors may be accomplished by any suitable technique which cleaves the chosen vector at an appropriate site or sites and results in at least one operable expression cassette containing the HSA structural gene being present in the vector. Ligation of the HSA structural gene may be accomplished by any appropriate ligation technique such as utilizing T4 DNA ligase.

The initial selection, propagation, and optional amplification of the ligation mixture of the HSA structural gene and a vector is preferably performed by transforming the mixture into a bacterial host such as *E. coli* (although the ligation mixture could be transformed directly into a yeast host but, the transformation rate would be extremely low). Suitable transformation techniques for *E. coli* are well known in the art. Additionally, selection markers and bacterial origins of replication necessary for the maintenance of a vector in a bacterial host are also well known in the art. The isolation and/or purification of the desired plasmid containing the HSA structural gene in an expression system may be accomplished by any suitable means for the separation of plasmid DNA from the host DNA. Similarly the vectors formed by ligation may be tested, preferably after propagation, to verify the presence of the HSA gene and its operable linkage to a regulatory region and a 3' termination sequence. This may be accomplished by a variety of techniques including but not limited to endonuclease digestion, gel electrophoresis, or Southern hybridization.

Transformation of plasmids or linear vectors into yeast hosts may be accomplished by suitable transformation techniques including but not limited to those taught by Cregg and Barringer, U.S. Pat. No. 4,929,555; Hinnen et al., *Proc. Natl. Acad. Sci.* 75, (1978) 1929; Ito et al., *J. Bacteriol.* 153, (1983) 163; Cregg et al. *Mol. Cell Biol.* 5 (1985), pg. 3376; D. W. Stroman et al., U.S. Pat. No. 4,879,231, issued Nov. 7, 1989; or Sreekrishna et al., *Gene*, 59 (1987), pg. 115. Preferable for the practice of this invention is the transformation technique of Cregg et al. (1985). It is desirable for the practice of this invention to utilize an excess of linear vectors and select for multiple insertions by Southern hybridization.

The yeast host for transformation may be any suitable methylotrophic yeast. Suitable methylotrophic yeasts include but are not limited to yeast capable of growth on methanol selected from the group consisting of the genera Hansenula and Pichia. A list of specific species which are exemplary of this class of yeasts may be found in C. Anthony, *The Biochemistry of Methylotrophs*, 269 (1982). Presently preferred are methylotrophic yeasts of the genus Pichia such as the auxotrophic *Pichia pastoris* GS115 (NRRL Y-15851); *Pichia pastoris* GS190 (NRRL Y-18014) disclosed in U.S. Pat. No. 4,818,700; and *Pichia pastoris* PPF1 (NRRL Y-18017) disclosed in U.S. Pat. No. 4,812,405. Auxotrophic *Pichia pastoris* strains are also advantageous to the practice of this invention for their ease of selection. It is recognized that wild type *Pichia pastoris* strains (such as NRRL Y-11430 and NRRL Y-11431) may be employed with equal success if a suitable transforming marker gene is selected, such as the use of SUC2 to transform *Pichia pastoris* to a strain capable of growth on sucrose or an antibiotic resistance marker is employed, such as G418.

Transformed *Pichia pastoris* cells can be selected for by using appropriate techniques including but not limited to culturing previously auxotrophic cells after transformation in the absence of the biochemical product required (due to the cell's auxotrophy), selection for and detection of a new phenotype ("methanol slow"), or culturing in the presence of an antibiotic which is toxic to the yeast in the absence of a resistance gene contained in the transformant.

Isolated transformed *Pichia pastoris* cells are cultured by appropriate fermentation techniques such as shake flask fermentation, high density fermentation or the technique disclosed by Cregg et al. in, *High-Level Expression and Efficient Assembly of Hepatitis B Surface Antigen in the Methylotrophic Yeast, Pichia Pastoris* 5 Bio/Technology 479 (1987). Isolates may be screened by assaying for HSA production to identify those isolates with the highest HSA production level.

The cultivation of transformed *Pichia pastoris* can be conducted in an aqueous continuous or batch-fed manner, utilizing a variety of carbon-energy sources and/or nutrient sources. For the practice of the present invention, batch-fed fermentation is preferred. Suitable carbon-energy sources for growing *Pichia pastoris* include but are not limited to the carbon-energy source selected from the group consisting of methanol, glycerol, sorbitol, glucose, fructose and combinations of any two or more thereof. Preferred carbon-energy sources for growing *Pichia pastoris* are carbon-energy sources selected from the group consisting of methanol, glycerol, and combinations thereof. A suitable nutrient source or media for *Pichia pastoris* would include at least one nitrogen source, at least one phosphate source, at least one source of minerals such as iron, copper, zinc, magnesium, manganese, calcium, and other trace elements, and vitamins (such as biotin, pantothenic acid, and thiamine as required).

Suitable sources of at least one carbon-energy source and nutrients can be obtained from a variety of sources or may consist of a single source. However, preferred are at least one carbon-energy source and/or nutrient sources which have a defined character. One carbon-energy source and/or nutrient composition which has proven effective is:

TABLE II

| Carbon-Energy Source and Nutrients | |
|---|---|
| Component per Liter of Water | |
| Carbon-energy Source (glycerol) | 50.0 g/l |
| $H_3PO_4$ (85%) | 21 ml/l |
| $CaSO_4.2H_2O$ | 0.9 g/l |
| $K_2SO_4$ | 14.28 g/l |
| $MgSO_4.7H_2O$ | 11.7 g/l |
| KOH | 3.9 g/l |
| Peptone | 10.0 g/l |
| [1]Yeast Extracts | 5.0 g/l |
| [2]Minerals and Trace Metals | 1.0 ml/l |

[1]Yeast extract is Amberex TM 1003 which is available from and a trademark of Universal Foods Corporation. Milwaukee. Wisconsin.
[2]Minerals and trace metals are $FeSO_4.7H_2O$ 65.0 g/l, $CuSO_4.5H_2O$ 6.0 g/l, $ZnSO_4.7H_2O$ 20 g/l, $MnSO_4$ 3.0 g/l and $H_2SO_4$ 5.0 ml/l The yeast extracts utilized in the present invention include but are not limited to yeast extracts selected from the group consisting of Amberex TM 1003 and Bacto TM Yeast Extract (Difco Laboratories Incorporated). Alternatively, corn steep liquor could be used to replace yeast extracts as a source of nitrogen.

Trace metals utilized in the present invention are those trace metals generally utilized in the yeast growth provided in an amount sufficient to not limit the growth rate or HSA production of *Pichia pastoris* which include but are not limited to trace metals selected from the group consisting of cobalt, molybdenum, iron, copper, zinc, and manganese.

The fermentation temperature should generally range from about 20° C. to about 35° C. and preferably should be about 30° C.

The dissolved oxygen content in the fermentation vessel where the fermentation is conducted in a batch-fed manner may range from about 20 percent to about 80 percent of saturation and preferably will range from about 30 percent to about 60 percent of saturation.

After the *Pichia pastoris* strains transformed with a vector containing the HSA structural gene have been cultivated to a high density, the transformed strains should then be induced to express HSA at a pH of from about 5.7 to about 6.0. For example, if this technique is employed with a strain transformed with a linear expression cassette containing a methanol inducible regulatory region, the culture would first be grown to the desired density on minimal salts, biotin and 5 percent glycerol by weight. The pH should be adjusted to 5.8 (with ammonia) with a temperature of about 30° C. and a dissolved oxygen concentration of about 20 percent of saturation. After the glycerol is exhausted, the promoter would be induced by beginning a slow methanol feed. The fed should provide methanol to the culture at a rate at least sufficient to maintain the viability of the culture but the maximum methanol concentration in contact with the culture should be no more than about 5.0 percent by weight. The HSA secretion can be monitored during the methanol feeding by sampling the HSA present in the cell free broth. Suitable test for quantifying the amount of HSA produced are known to those skilled in the art, such as running polyacrylamide gels. The methanol feed should be continued until the HSA concentration reaches an acceptable level. Generally, the HSA production will peak after about 120 hours on methanol feed.

If the transformed *Pichia pastoris* cells are grown in shake tubes or shake flasks instead of pH controlled fermenter, additional steps should be taken to assure the maximum yields of secreted proteins, such as HSA. Specifically, it is recommended that the media used be modified from that used in fermenter to a complex media and the aeration be increased. The complex media utilized in the shake flasks and shake tubes should contain added amino acids. The amino acids may be in a defined media containing glutamic acid, methionine, lysine, leucine, isoluecine and other amino acids or through a complex media supplement, such as yeast extract or casamino acids. The relative concentrations of the added amino acids should generally range from about 2.5 mg/liter to about 10 mg/liter with the preferred range being from about 4 mg/liter to about 6 mg/liter of glutamic acid, methionine, lysine, leucine and isoluecine and from about 0.5 mg/liter to about 3 mg liters of the remaining amino acid (however, histidine may be omitted entirely from the added amino acids). If yeast extract is used in place of the added amino acids, it is preferred that the yeast extract be provided in a concentration of in the range of from about 1 g/liter to about 15 g/liter be utilized in the media and most preferably the yeast extract will be provided in a concentration of 10 g/liter. It has also been found desirable to add peptone to the media to improve secretion in shake tubes and shake flasks. For optimum secretion that peptone be used with the yeast extract in a concentration of from in the range of from about 1 g/liter to about 50 g/liter, and most preferably in a concentration of about 20 g/liter. As a guideline, it is generally recommended that the peptone concentration be twice the yeast extract concentration.

Aeration in shake flask and shake tube growth of transformed *Pichia pastoris* appears to be an important parameter in obtaining optimum secretion. To insure adequate aeration, it is recommended that shake tube or flask have a large aperture covered with an air permeable cap. Suitable air permeable caps can be made of a loose filter material, such as cheese cloth. One suitable shake flask for this invention is the Tunair shake flask. Generally, low baffle shake flasks are also recommended to avoid excessive foaming. Shaker speed for aeration is recommended to be in the range of from about 250 rpms to about 300 rpms.

After a suitable cell density is achieved in the shake flask or shake tube, the cells may be recovered then resuspended in a medium containing methanol in place of the carbon source used for growth to induce the secretion of protein. The flask or shake tubes may then be monitored on a regular basis to determine when the desired level of production has been achieved.

The invention will now be described in greater detail in the following non-limiting examples.

EXAMPLES

General information pertinent to the Examples:

Stains

*Pichia pastoris* GS115 (his 4) NRRL Y-15851
*E. coli* DG75' (hsd1, leu6, lacY, thr-1, supE44, tonA21, lambda−).

Buffers, Solutions and Media

The buffers, solutions, and media employed in the following examples have the compositions given below:

| | |
|---|---|
| $dH_2O$ | deionized $H_2O$ that has been treated with a milli-Q (Millipore) reagent water system. |
| 1$\underline{M}$ Tris buffer | 121.1 g Tris base in 800 mL of $H_2O$; adjust pH to the desired value by adding concentrated (35%) aqueous HCl; allow solution to cool to room temperature before final pH adjustment, dilute to a final volume of 1 L. |
| TE buffer | 1.0 m$\underline{M}$ EDTA in 0.01 $\underline{M}$ (pH 8.0) Tris bufffer |
| SED | 1 $\underline{M}$ sorbitol<br>25 m$\underline{M}$ EDTA<br>50 m$\underline{M}$ DTT, added prior to use<br>--adjust to pH 8 |
| SCE | 9.1 g sorbitol<br>1.47 g Sodium citrate<br>0.168 g EDTA<br>--pH to 5.8 with HCl in 50 ml $dH_2O$ and autoclave |
| CaS | 1 $\underline{M}$ sorbitol<br>10 m$\underline{M}$ $CaCl_2$<br>--filter sterilize |
| SOS: | 1 M sorbitol<br>0.3x YPD<br>10 mM $CaCl_2$ |
| PEG | 20% polyethylene glycol-3350<br>10 m$\underline{M}$ $CaCl_2$<br>10 m$\underline{M}$ Tris-HCl (pH 7.4)<br>--filter sterilize |
| Solution A | 0.2 M Tris-HCl (pH 7.5)<br>0.1 M $MgCl_2$<br>0.5 M NaCl<br>0.01 M dithiothreitol (DTT) |
| Solution B | 0.2 M Tris-HCl (pH 7.5)<br>0.1 M $MgCl_2$<br>0.1 M DTT |
| Solution C (keep on ice) | 4 µl solution B<br>4 µl 10 mM dATP<br>4 µl 10 mM dTTP<br>4 µl 10 mM dGTP<br>4 µl 10 mM dCTP<br>4 µl 10 mM ATP<br>5 µl $T_4$ ligase (2 U/µl)<br>12 µl $H_2O$<br>Recipe for Solution C was modified from Zoller & Smith |
| LB Broth, 1 liter | 5.0 g yeast extract<br>10.0 g tryptone |

| | |
|---|---|
| 10X Transfer Buffer | 5.0 g NaCl<br>96.8 g Trizma Base<br>9.74 g glycine<br>water to 1 liter |
| Ligation Buffer | 50 mM Tris-HCl (pH 7.4)<br>10 mM MgCl$_2$<br>10 mM dithiothreitol<br>1 mM ATP |
| Phosphatase Buffer | 50 mM Tris-HCl (pH 9.0)<br>1 mM MgCl$_2$<br>1 mM ZnCl$_2$<br>1 mM spermidine |
| Bsu36I buffer | 100 mM NaCl<br>10 mM Tris-HCl (pH 7.4)<br>10 mM MgCl$_2$<br>100 µg/ml BSA |
| Csp45I buffer | 60 mM NaCl<br>10 mM Tris-HCl, pH 7.5<br>7 mM MgCl$_2$<br>100 µg/ml BSA |
| REact 1 buffer | 50 mM Tris-HCl, pH 8.0<br>10 mM MgCl$_2$<br>100 µg/ml BSA |
| REact 2 buffer | REact 1 buffer + 50 mM NaCl |
| REact 3 buffer | REact 1 buffer + 100 mM NaCl |
| HS buffer | 50 mM Tris-HCl, pH 7.5<br>10 mM MgCl$_2$<br>100 mM NaCl<br>1 mM DTT<br>100 µg/ml BSA |
| 10X Basal Salts | 42 mls Phosphoric Acid, 85%<br>1.8 g Calcium Sulfate.2H$_2$O<br>28.6 g Potassium Sulfate<br>23.4 g Magnesium Sulfate.7H$_2$O<br>6.5 g Potassium Hydroxide |
| Ptm$_1$ Trace Salts Solution | 6.0 g Cupric Sulfate.5H$_2$O<br>0.08 g Sodium Iodide<br>3.0 g Manganese Sulfate.H$_2$O<br>0.2 g Sodium Molybdate.H$_2$O<br>0.02 g Boric Acid<br>0.5 g Cobalt Chloride<br>20.0 g Zinc Chloride<br>65.0 g Ferrous Sulfate.H$_2$O<br>0.20 g Biotin<br>5.0 mls Sulfuric Acid |
| YPD (yeast extract peptone dextrose medium) | 10 g bacto yeast extract<br>20 g peptone<br>10 g dextrose<br>water to 1 liter |
| MGY (minimal glycerol medium) | 13.4 g yeast nitrogen base with ammonium sulfate, and without amino acids<br>400 µg biotin<br>10 ml glycerol<br>water to 1 liter |
| MM (minimal methanol medium) | Same as MGY, except that 5 ml methanol is used in the place of 10 ml glycerol. |
| SDR (supplemented dextrose regeneration medium): | 13.4 g yeast nitrogen base with ammonium sulfate and without amino acids<br>400 µg biotin<br>182 g sorbitol<br>10 g glucose<br>2 g Histidine assay mix (Gibco)<br>50 mg glutamine<br>50 mg methionine<br>50 mg lysine<br>50 mg leucine<br>50 mg isoleucine<br>10 g agarose<br>water to 1 liter |
| BMGR (Buffered minimal glycerol-enriched medium) | 100 ml/liter Potassium phosphate buffer, (pH 6.0)<br>13.4 grams/liter Yeast nitrogen base with ammonium sulfate<br>400 µg/liter biotin<br>10 ml/liter glycerol<br>Amino acids<br>glutamic acid, methionine, lysine, leucine and isoleucine: each at 5 mg/liter;<br>all the other amino acids except histidine at 1 mg/liter<br>Nucleotides<br>adenine sulfate, guanine hydrochloride, uracil, and xanthine, each at 40 µg/liter<br>Vitamins<br>thiamine hydrochloride, riboflavin, and calcium pantothenate, each at 2 µg/liter;<br>pyridoxide hydrochloride and nicotinic acid, each at 4 µg/liter;<br>pyridoxamine hydrochloride and pyridoxal hydrochloride, each at 1 µg/liter;<br>para-amino benzoic acid at 0.3 µg/liter;<br>folic acid at 0.03 µg/liter<br>Trace minerals<br>magnesium sulfate at 800 µg/liter;<br>ferrous sulfate at 40 µg/liter;<br>manganese sulfate at 80 µg/liter;<br>sodium chloride at 40 µg/liter |
| BMGY (Buffered minimal glycerol-complex medium) | 100 ml/liter potassium phosphate buffer, (pH 6.0)<br>13.4 grams/liter yeast nitrogen base with ammonium sulfate and without amino acids<br>biotin at 400 µg/liter<br>glycerol at 10 ml/liter<br>yeast extract at 10 g/liter<br>peptone at 20 g/liter |
| BMMR (Buffered minimal methanol-enriched medium) | Same as BMGR, with the exception that 5 ml methanol/liter is added in the place of glycerol |
| BMMY (Buffered minimal methanol-complex medium) | Same as BMGY, with the exception that 5 ml methanol/liter is added in the place of glycerol |

Techniques

Suitable techniques for recombinant DNA lab work may be found in many different references including but not limited to: *Methods in Enzymology*, (Orlando, Fla.: Academic Press, Inc.), particularly Volume 152, published as, *Guide to Molecular Cloning Techniques*, by Berger and Kimmel (Orlando, Fla.: Academic Press, Inc., 1987) and *Molecular Cloning/A Laboratory Manual*, by Sambrook et al., 2d ed. (Cold Spring Harbor Laboratory Press, 1989) and which are all hereby incorporated by reference.

EXAMPLE I

Construction of 5'-exact HSA expression vector pHSA313

The pHSA313 vector was constructed to provide a vector with an exact linkage between the 3' end of the native AOX1 5' regulatory region (promoter) and the start codon of the HSA structural gene.

A. Creation of pHSA113ΔCla

About 200 ng of pHSA113, disclosed in European Patent Application 0 344 459 which is herein incorporated by reference, (see FIG. 7) was digested at 37° C. for 1 hour with 1 unit of ClaI in 20 µl of REact 1 buffer. The digestion mixture was brought to 100 µl with water and extracted once with an equal volume of phenol:chloroform:isoamyl alcohol (25:24:1 V/V), followed by extracting the aqueous layer with an equal volume of chloroform:isoamyl alcohol (24:1). The DNA in the aqueous phase was precipitated by adjusting the NaCl concentration to 0.2M and adding 3 volumes of cold ethanol. The mixture was allowed to stand on ice (4° C.) for 10 minutes and the DNA precipitate was collected by centrifugation for 30 minutes at 10,000×g in a microfuge at 4° C. The DNA pellet was washed 2 times with 70% aqueous cold ethanol. The washed pellet was vacuum dried and dissolved in 10 µl water to which 2 µl of 10×ligation buffer, 2 µl of 1 mg/ml BSA, 6 µl of water and 1 unit T$_4$ DNA ligase were added. The mixture was incubated overnight at 4° C. and a 10 µl aliquot was used to transform E. coli DG75' (Maniatis, et al.) to obtain pHSA113ΔCla, which represents the deletion of HIS4 and 3'AOX1, along with small stretches of pBR322 sequences used to link these sequences. The deletion of the HIS4, 3' AOX1 and pBR322 sequences removes one of two Csp45I sites present in the pHSA113 vector. The remaining Csp45I site is in the AOX1 5' regulatory region (promoter).

B. Creation of pXHSA113ΔCla

Digest 5 μg of pHSA113ΔCla for 1 hour at 37° C. with 10 units of BstEII in 100 μl of REact 2 buffer. The digestion mixture was extracted with phenol and precipitated as detailed in step A. The DNA precipiate was dissolved in 100 μl of Csp45I buffer and digested at 37° C. for 2 hours in the presence of 10 units of Csp45I. The digested DNA was then phenol extracted and precipitated as described in step A. The DNA precipitate was dissolved in 20 μl of water and 10 μl aliquots were loaded on 2 neighboring wells of a 0.9% agarose gel. Following electrophoresis, the gel portion corresponding to one of the lanes was stained and this was used to locate the position of the Csp45I-BstEII fragment of pHSA113ΔCla in the unstained lane. The gel portion containing the larger Csp45I-BstEII fragment was excised out and the DNA in the gel was electroeluted into 500 μl of 5 mM EDTA, pH 8.0. The DNA solution was phenol extracted as detailed in step A and the DNA precipitate was dissolved in 100 μl water. The larger Csp45I-BstEII fragment was then ligated with the BstEII-Csp45I oligonucleotide linker described below. An aliquot (10 μl) was ligated overnight at 4° C. with 20 ng of annealed linker oligonucleotides 5'-CGAAACG ATG AAG TGG (SEQ ID NO:4) and 5'-GTTACC-CACTTCATCGTTT (SEQ ID NO:5) in 20 μl ligase buffer containing 100 μg/ml BSA and 1 unit of T4 DNA ligase. The ligation mixture was used to transform E. coli DG75' to obtain pXHSA113ΔCla. The pXHSA113ΔCla vector by virtue of the linker described above has an exact linkage between the 3' end of the native AOX1 5' regulatory region (promoter) and the HSA ATG start codon with no extraneous DNA sequences.

C. Creation of pHSA313

1 μg of pXHSA113ΔCla was digested for 4 hours at 37° C. with ClaI in 100 μl of REact 1 buffer. Following digestion the reaction mixture was adjusted to alkaline phosphatase buffer conditions and treated with 10 units of calf intestinal alkaline phosphatase in a 200 μl reaction volume for 30 minutes at 37° C. Phosphatase treatment was terminated by phenol extraction and the DNA was precipitated and dissolved in water at a concentration of approximately 10 ng/μl as described in step A and stored at −20° C.

1 μg of pA0807N (FIG. 8, construction of which is described in European Patent Application 0 344 459) was digested for 4 hours at 37° C. with PstI in 100 μl of REact 2 buffer. The digested DNA adjusted to alkaline phosphatase buffer conditions and treated with 10 units of calf intestinal alkaline phosphatase in a 200 μl reaction volume for 15 minutes at 55° C. At the end of the 15 minutes another 10 units of phosphatase was added and incubated for 15 minutes. Phosphatase treatment was terminated by phenol extraction and the DNA was precipitated as described in step A. DNA was digested for 4 hours at 37° C. with 5 units of ClaI in 100 μl buffer containing 100 μg/ml BSA, followed by phenol extraction and precipitation of DNA as outlined in step A. The DNA precipitate was dissolved in water at a concentration of approximately 20 ng/μl.

Approximately 100 ng (10 μl) of ClaI cleaved-phosphatased pXHSA113ΔCla was mixed with approximately 80 ng of PstI digested-phosphatased and ClaI-cleaved pA0807N (4 μl), 4 μl of 5× ligase buffer, 2 μl of 1 mg/ml BSA and ligated overnight at 4° C. using 1 unit of T4 DNA ligase. The ligation mixture was used to transform E. coli DG75' to obtain pHSA313. The pHSA313 plasmid from this ligation contains the complete pXHSA113ΔCla sequence linked to the HIS4 gene and the AOX1 3' second insertable sequence derived from A0807N. The relative orientation of the components of the pHSA313 plasmid is the same as that shown in FIG. 7 for plasmid pHSA113.

EXAMPLE II

Construction of Expression Vector pPGP1

The expression vector pPG1 was constructed in the following manner. pXHSA113ΔCla (see Example I) was digested with Bsu36I and PvuII (partial) and the vector backbone was isolated. An HSA structural gene on a PvuII-Bsu36I fragment analogous to the structural gene contained in pHSA113 (disclosed in European Patent Application 0 344 459) was ligated to this vector backbone to obtain pPGP1ΔCla. About 100 ng of pPGP1ΔCla was digested with ClaI at 37° C. for 1 hour. The DNA was recovered as in Example I. About 100 ng of pA0807N (shown herein in FIG. 8 and disclosed in European Patent Application 0 344 459) was digested with PstI, alkaline phosphatase treated and then digested with ClaI as detailed in Example I C. This fragment was then ligated to ClaI cleaned, alkaline phosphatase treated pPGP1ΔCla to obtain pPGPI. (GS115 pPGP1-9-6 is a clone which was obtained by transformation of Pichia pastoris GS115 with pPGP1 and this clone was used in fermentation).

EXAMPLE III

Construction of 5' and 3' exact HSA expression plasmid pHSA413

The pHSA413 vector was constructed to provide a vector with an exact linkage between the 3' end of the AOX1 5' regulatory region and the start codon fo the HSA structural gene as well as an exact linkage between the 5' end of the AOX1 3' termination sequence and the 3' end of the HSA structural gene.

A. Creation of pXXHSA113ΔCla

1 μg of pXHSA113ΔCla was digested for 4 hours at 37° C. with 10 units of EcoRI in 100 μl REact 3 buffer. The digestion mixture was phenol extracted and DNA precipitated as detailed in Example VI. DNA precipitate was dissolved in 20 μl water and digested for 1 hours at 37° C. with 20 units of Bsu36I in 100 μl of Bsu36I buffer. The digestion mixture was phenol extracted, DNA precipitated and dissolved in 100 μl of water as detailed in Example VI. Approximately 100 ng of EcoRI and Bsu36I-cleaved DNA was mixed with 10 ng of annealed oligonucleotides 5'-TTAGGCT-TATAAG (SEQ ID NO:6) and 5'-AATTCT-TATAAGCC (SEQ ID NO:7) and ligated overnight at 4° C. in 20 μl of T4 DNA ligase buffer containing 100 μg/ml BSA and 10 units of T4 DNA ligase. The ligation mixture was used to transform E. coli to obtain pXXHSA113ΔCla. In this plasmid the sequence between Bsu36I and EcoRI (SEQ ID NO:8) present in pxHSA113ΔCla shown below

```
Bsu36I
5'CCT T AGGC T TAT AACAT CT CT ACAT T T AAAAGCAT CT CAGCCT ACCAT G

AGAAT AAGAGAAAGAAAAT GAAGAT CA
AAAGCT T AT T CAT CT GT GT T T T CT T T T T CGT T GGT GT AAAGCCAACACCCT

GT CT AAAAAACAT AAAT T T CT T T AAT C
AT T T T GCCT CT T T T T CT CT GT GCT T CAAT T AAT AAAAAAT GGAAAGAAT CT

AAAAAAAAAAAAAAAAAAAGGAATTC
                                            EcoRI is replaced by 5'CC TTA GGC TTA TAA GAATTC (SEQ ID NO: 9)
              Bsu36I              EcoRI
```

B. Creation of pHSA413

1 μg of pXXHSA113ΔCla was digested for 4 hours at 37° C. with ClaI in 100 μl of REact 1 buffer. Following digestion the reaction mixture was adjusted to alkaline phosphatase buffer conditions and treated with 10 units of calf intestinal alkaline phosphatase in 200 μl reaction volume for 30 minutes at 37° C. Phosphatase treatment was terminated by phenol extraction and the DNA was precipitated and dissolved in water at a concentration of approximately 10 ng/μl as described in step A and stored at −20° C.

Approximately 100 ng (10 μl) of ClaI cleaved-phosphatased pXXHSA113ΔCla was mixed with approximately 80 ng (4 μl) of PstI digested phosphatased and ClaI-cleaved pA0807N (see paragraph 2 in step 3 of Example VI), 4 μl of 5×ligase buffer, 2 μl of 1 mg/ml BSA and ligated overnight at 4° C. using 1 unit of T4 DNA ligase. The ligation mixture was used to transform *E. coli* DG75' to obtain pHSA413. The pHSA413 plasmid from this ligation contains the complete pXHSA113ΔCla sequence linked to the HIS4 gene and the AOX1 3' second insertable sequence derived from A0807N. The relative orientation of the components of the pHSA413 plasmid is the same as that shown in FIG. 7 for plasmid pHSA113.

EXAMPLE IV

Transformation of *Pichia pastoris* with pHSA313, pHSA413, and pPGP1

A. Vector preparation

About 10 μg each of pHSA313, pHSA413, pPGP1, and pA0807N (negative control) were digested for 12 hours at 37° C. in 200 μl of HS buffer with 50 units of NotI. The digested DNA samples were phenol extracted, precipitated as described in Example VI, dissolved in 20 μl of CaS, and were then used for transformation of *Pichia pastoris* GS115. About 10 μg each of pHSA313, pHSA413, and pA0807N were also digested with 20 units of SstI for 12 hours at 37° C. in 200 μl of REact 2 buffer containing 100 μg/ml of BSA. The digested DNA samples were extracted with phenol, precipitated as described in Example VI and dissolved in 20 μl of CaS.

B. Cell Growth

*Pichia pastoris* GS115 (NRRL Y-15851) was inoculated into about 10 ml of YPD medium and shake cultured at 30° C. for 12-20 hours. 100 ml of YPD medium was inoculated with a seed culture to give an $OD_{600}$ of about 0.001. The medium was cultured in a shake flask at 30° C. for about 12-20 hours. The culture was harvested when the $OD_{600}$ was about 0.2–0.3 by centrifugation at 1555 g for 5 minutes using a Sorvall RB5C.

C. Preparation of Spheroplasts

The cells were washed in 10 ml of sterile water, and then centrifuged at 1500 g for 5 minutes. (Centrifugation is performed after each cell wash at 1500 g for 5 minutes using a Sorvall RT6000B unless otherwise indicated.) The cells were washed once in 10 ml of freshly prepared SED, once in 10 ml of sterile 1M sorbitol, and finally resuspended in 10 ml of SCE buffer. 7.5 μl of 3 mg/ml Zymolyase (100,000 units/g, obtained from Miles Laboratories) was added to the cell suspension. The cells were incubated at 30° C. for about 10 minutes. (A reduction of 60% in $OD_{600}$ in 5% SDS can be utilized as a correct time marker.) The spheroplasts were washed in 10 ml of sterile 1M sorbitol by centrifugation at 700 g for 5-10 minutes. 10 ml of sterile CaS was used as a final cell wash, and the cells were centrifuged again at 700 g for 5-10 minutes and then resuspended in 0.6 ml of CaS.

D. Transformation

*Pichia pastoris* GS115 cells were transformed with 10 μg of linearized DNA (see step A) using the spheroplast transformation technique of Sreekrishna et al, *Gene* 59, 115-125 (1987). DNA samples were added (up to 20 μl volume) to 12×75 mm sterile polypropylene tubes. (DNA should be in a suitable buffer such as TE buffer or CaS.) 100 μl of spheroplasts were added to each DNA sample and incubated at room temperature for about 20 minutes. 1 ml of PEG solution was added to each sample and incubated at room temperature for about 15 minutes and centrifuged at 700 g for 5-10 minutes. SOS (150 μl) was added to the pellet and incubated for 30 minutes at room temperature. Finally 850 μl of 1M sorbitol was added.

E. Regeneration of Spheroplasts

A bottom agarose layer of 20 ml of regeneration agar SDR was poured per plate at least 30 minutes before transformation samples were ready. In addition, 8 ml aliquots of regeneration agar were distributed to 15 ml conical bottom Corning tubes in a 45° C. water bath during the period that transformation samples were in SOS. Aliquots of 50 or 250 μl of the transformed sample was added to the 8 ml aliquots of molten regeneration agar held at 45° C. and poured onto plates containing the solid 20 ml bottom agar layer. The plates were incubated at 30° C. for 3-5 days.

F. Selection of Transformants

Transformants were selected for by culturing on SDR, a media lacking histidine. The colonies which grew in the absence of histidine were also screened for "methanol-slow" phenotype, indicating displacement of the AOX1 structural gene by the NotI DNA fragment) in the case of transformants obtained using NotI linearized vectors. Several transformed GS115 cells showing "methanol-normal" (those obtained with SstI linearized DNA) and methanol-slow were then cultured and assayed for the production of HSA.

EXAMPLE V

Methanol Induced Secretion of HSA in *Pichia pastoris* Integrative Transformants

*Pichia pastoris* GS115 strains transformed with pHSA313, pHSA413, and pPGP1 were analysed for HSA secretion in shake tube cultures. Both methanol-slow and methanol-normal strains were used. In each case 36 independent clones were studied. Transformants obtained with pA0807N served as negative controls. A protocol was developed to ensure efficient secretion and stable accumulation of HSA in the culture medium.

Cells were grown to saturation in 10 ml BMGR or BMGY, and were placed in 50 ml tubes (2-3 days). The cells would be in the range of 10-20 $A_{600}$ units. The cells were harvested, the supernatant liquid was discarded, and then the pellet was resuspended in 2 ml of BMMR or BMMY. The tube was covered with a sterile gauze (cheese cloth) instead of a cap. The tube(s) were then returned to a 30° C. shaker. At the end of 2-3 days, the cells were pelleted, and the supernatant assayed for product. The pellets could be resuspended with fresh medium and returned to the shaker for renewed secretion. With Pichia-HSA strains, 10 μl of media supernatant was sufficient for analysis by SDS-PAGE followed by Coomassie staining. Under these conditions a single band of 67 kD corresponding to HSA was observed. There was no significant difference between the expression levels of GS115/pHSA313 vs GS115/pHSA413 transformants, suggesting that deleting the 3' untranslated sequences from the HSA gene present in pHSA313 did not significantly affect expression levels. No significant difference in the HSA expression level was observed between methanol-slow vs methanol-normal transformants, suggesting that disruption of AOX1 was not essential for efficient HSA expression. As expected, HSA was absent in both the culture medium and the cell extract of GS115/pA0807N transformants (negative control). Clonal variants were selected which demonstrated increased levels of HSA secretion.

EXAMPLE VI

Batch-Fed Fermentation of Mut *Pichia pastoris* for Production of HSA

*Pichia pastoris* GS115:pHSA 413-6 and pPGP1-9-6 were inoculated into two 20 liter Biolafitte fermenters with an 8.5 l working volume. The inoculum was prepared in the following manner: a culture was grown on a YM plate and then transferred to 100 ml YM broth in a shake flask and grown for about 24 hours. 50 mls of this culture was transferred to 1 liter of YM broth in a shake flask and also grown for about 24 hours. 1 liter of this was then transferred to 8.5 liters of fermenter medium in the Biolafitte fermenter. Fermentor medium consisted of Minimal salts + biotin + 5 percent glycerol. Batch growth conditions included the following: pH=5.8 (controlled with NH₃), temperature=30° C., and percent dissolved oxygen greater than 20 percent air saturation.

Glycerol exhaustion was complete after about 24 hours, at which time a slow methanol feed was begun at a rate of 10-15 ml/hr. The methanol concentration was monitored in the fermenter and the feed rate was adjusted to maintain a concentration of 0.5-0.9 percent of methanol in the broth.

Secreted HSA in the media was measured quantitatively by densitometry of Coomassie blue stained polyacrylamide gels containing SDS (SDS-PAGE). Areas were referenced to a series of known weights of authentic HSA run on the same SDS-PAGE gels. The data from these gels is included in Tables I and II.

The following Table illustrates the effect of changes in pH on the amount of HSA produced:

TABLE III

| Production of HSA by Batch-Fed Fermentation | | | |
| --- | --- | --- | --- |
| Run | Strain | pH | HSA g/l |
| 1 | GS115:pPGP1-9-6 | 5.09-5.32 | 0.71 |
| 2 | GS115:pPGP1-9-6 | 5.22 | 0.81 |
| 3 | GS115:pPGP1-9-6 | 5.91 | 1.28 |
| 4 | GS115:pPGP1-9-6 | 5.78 | 1.59 |
| 5 | GS115:pPGP1-9-6 | 5.78 | 1.98 |
| 6 | GS115:pPGP1-9-6 | 5.79 | 1.32 |

The following Table illustrates the level of HSA production which can be achieved at higher pH levels:

TABLE IV

| Production of HSA by Batch-Fed Fermentation | | | | | |
| --- | --- | --- | --- | --- | --- |
| Run | Strain | pH | Hours MeOH | Dry Cell Wt. | HSA Broth g/l |
| 1 | GS115:pHSA 413-6 | 5.79 | 101 | ND | 2.13 |
| 2 | GS115:pHSA 413-6 | 5.85 | 237 | 101 | 3.39 |
| 3 | GS115:pHSA 413-6 | 5.85 | 265 | 98 | 2.70 |
| 4 | GS115:pHSA 413-6 | 5.97 | 258 | 117 | 2.90 |

ND = Not Determined

EXAMPLE VII

Protocol for Shake Tube and Shake Flask Secretion of Proteins from *P. pastoris*

For efficient secretion and stable accumulation of HSA in shake tubes and shake flasks it is necessary to use a pH of 5.7-6.4 instead of 5.0 or 5.2 for the fermenter media, to add small amounts yeast extract (0.5-0.1%) and peptone (0.1-0.2%) to the fermenter medium and to start inducing expression at a low cell density (20-25 gram dry cell weight/liter). Using these techniques, we have developed a protocol that permits efficient secretion of HSA from cells grown in shake tubes and flasks. We believe that this protocol is applicable in general to secretion of proteins from *Pichia pastoris*.

Shake Tube

Grow cells to saturation in 10 ml BMGR or BMGY placed in 50 ml tube (2-3 days). The $A_{600}$ of cells will be in the range of 10-20. Harvest cells, discard the supernatant liquid and resuspend the pellet with 2 ml of BMMR or BMMY. Cover the tube with a sterile gauze or cheese cloth instead of the cap, Return the tube(s) to the shaker and maintain the shaker at about 30° C. At the end of 2-3 days, pellet cells, and analyze supernatant for product. The pellet can be resuspended with fresh media and returned to shaker for renewed secretion. With Pichia-HSA strains, 10 u1 of media supernatant is sufficient for analysis by SDS-PAGE followed by Coomassie staining. Under these conditions, a single band corresponding to HSA size (67 kD) is observed.

Shake Flask

Grow cells as described above in 1 liter of medium (BMGY or BMGR) in a 2 liters flask. Harvest cells and suspend with 50–75 ml of BMMR or BMMY in a fermenter flask (Tunair ™ shake-flask fermentation system, Research Products International Corporation) or a baffled flask covered with cheese cloth. Return to the shaker at 30° C. and induce for 2–4 days. At the end of 2–4 days the cells are pelleted and the supernatant is analyzed for product. Shake tubes secretion can be re-initiated by resuspending the pelleted cells in fresh media.

---

That which is claimed is:

1. An improved process for the secretion of a HSA protein in transformed *Pichia pastoris* cells comprising:
   (a) cultivating in a fermentation broth said transformed *Pichia pastoris* cells which express a HSA structural gene encoding a native HSA secretion signal sequence and a mature HSA protein, wherein the native HSA signal sequence is operably linked to the sequence encoding the mature HSA protein, under conditions suitable for sustaining the viability of said transformed *Pichia pastoris* cells, under suitable conditions for the expression of said HSA protein by said *Pichia pastoris* cells, and
   (b) maintaining the pH of said fermentation broth at a pH in the range of from about 5.7 to about 6.4 contemporaneously with the expression of a HSA protein.

2. The process of claim 1 wherein *Pichia pastoris* is transformed with a vector selected from the group consisting of a circular plasmid and a linear plasmid.

3. The process of claim 2 wherein the vector is a linear integrative site-specific vector.

4. The process of claim 3 wherein said linear integrative site-specific vector contains the following serial arrangement:
   (a) a first insertable DNA fragment,
   (b) at least one marker gene, and at least one expression cassette containing a HSA structural gene encoding a native HSA signal sequence and a mature HSA protein, operably linked to a *Pichia pastoris* AOX1 5' regulatory region and a 3' termination sequence, and
   (c) a second insertable DNA fragment;
      wherein the order of the marker gene and cassette of component (b) may be interchanged, and the first and second insertable DNA fragments employed are homologous with separate portions of the *Pichia pastoris* genome wherein the insertable fragments are in the same relative orientation as exist in the *Pichia pastoris* genome.

5. The process of claim 4 wherein the first insertable DNA fragment and the second insertable DNA fragment are obtained from the DNA sequence of a gene from *Pichia pastoris* selected from the group consisting of the AOX1 gene, the p40 gene, the DAS gene, the GAP gene, the PHO1 gene and the HIS4 gene.

6. The process of claim 4 wherein said marker gene is selected from the group consisting of HIS4 isolated from *Pichia pastoris*, ARG4 isolated from *Pichia pastoris*, SUC2 isolated from *Saccharomyces cerevisiae*, G418$^R$ gene of Tn903 and G418$^R$ gene of Tn601.

7. The process of claim 4 wherein said plasmid comprises:
   (a) the AOX1 5' regulatory region isolated from *Pichia pastoris* operably linked to
   (b) a structural gene for HSA encoding a native signal sequence for HSA and a mature HSA protein, wherein the HSA signal sequence is operably linked to the sequence encoding the mature HSA protein operably linked to (c) the 3' termination sequence of AOX1 isolated from *Pichia pastoris* operably linked to
(d) at least one marker gene, and
(e) a second DNA fragment which is about a 0.19 kilobase sequence of an autonomous replicating DNA sequence.

8. The process of claim 7 wherein said marker gene is HIS4.

9. The process of claim 1 wherein the transformed *Pichia pastoris* cells are grown in a batch-fed manner during the expression of HSA and the pH of the fermentation broth is maintained during expression of the heterologous protein in the range of from about pH 5.7 to about pH 6.0.

10. The process of claim 9 wherein the fermentation broth contains an effective amount of a suitable minimal salts mixture, growth factors and at least one suitable carbon source selected from the group consisting of methanol, glycerol, sorbitol, glucose, fructose and combinations of two or more thereof to maintain the viability of said transformed *Pichia pastoris* cells.

11. The process of claim 10 wherein after the fermentation broth's carbon source is consumed, the transformed *Pichia pastoris* cells are contacted with methanol wherein the methanol is provided at a rate sufficient to maintain the viability of the *Pichia pastoris* cells in contact therewith and the methanol concentration does not exceed about 5.0 percent by weight.

12. The process of claim 9 wherein the pH during the batch-fed growth of the *Pichia pastoris* cells is pH 5.8.

13. A process according to claim 1 wherein said fermentation broth containing the transformed *Pichia pastoris* cells is contacted with from 2.5 mg/liter to about 10 mg/liter of added amino acids selected from the group consisting of glutamic acid, methionine, lysine, leucine and isoleucine and from about 1 gram/liter to about 50 grams/liter of peptone when said secretion is carried out in a shake tube or shake flask.

14. The process of claim 13 wherein the amino acids are provided in the form of yeast extract at a concentration in the range of from about 1 g/liter to about 15 g/liter.

15. The process of claim 14 wherein the peptone is provided at a concentration of about 20 g/liter.

16. An improved process for the secretion of HSA in transformed cells of *Pichia pastoris* GS115 comprising:
(a) cultivating in a fermentation broth cells of *Pichia pastoris* GS115 which have been transformed with a linear integrative site-specific vector containing the following serial arrangement: a first insertable DNA fragment 5' AOX1 Promoter at least one expression cassette containing a HSA structural gene encoding a signal sequence and a mature HSA protein operably linked to a *Pichia pastoris* AOX1 regulatory region and an AOX1 termination sequence, at least one marker gene and a second insertable DNA fragment 3' to AOX1 termination sequence, under conditions suitable for sustaining the viability of said transformed cells of *Pichia pastoris* GS115, under suitable conditions for the expression of said HSA by said cells of *Pichia pastoris* GS115, and
(b) maintaining the pH of said fermentation broth at a pH in the range of from about 5.7 to about 6.4 contemporaneously with the expression of HSA protein.

* * * * *

UNITED STATES PATENT AND TRADEMARK OFFICE
CERTIFICATE OF CORRECTION

PATENT NO. : 5,330,901
DATED : July 19, 1994
INVENTOR(S) : William D. Prevatt, et al.

It is certified that error appears in the above-indentified patent and that said Letters Patent is hereby corrected as shown below:

Column 5, line 24: "NO." should read --No.--

Column 8, lines 43 & 50: "Amberex TM" should read --Amberex $^{TM}$--

Column 8, line 51: "Bacto TM" should read --Bacto $^{TM}$--

Column 13, line 65: before "buffer" insert --REact 1--

Column 14, line 20: "pPG1" should read --pPGP1--

Column 14, line 55: "hours" should read --hour--

Column 17, line 51: "Mut" should read --<u>Mut</u>--

Column 20, line 1: "Tunair TM" should read --Tunair $^{TM}$--

Column 22, line 26: "Lue" should read --Leu--

Column 28, line 60, Claim 7: "plasmid" should read --vector--

Signed and Sealed this

First Day of August, 1995

Attest:

BRUCE LEHMAN

Attesting Officer     Commissioner of Patents and Trademarks